United States Patent
Klimka et al.

(10) Patent No.: US 11,801,292 B2
(45) Date of Patent: Oct. 31, 2023

(54) **POLYPEPTIDE EPITOPES OF *S. AUREUS* AND RESPECTIVE MONOCLONAL ANTIBODIES FOR THE TREATMENT OF INFECTIONS AND IMMUNE-DIAGNOSIS**

(71) Applicants: Alexander Klimka, Cologne (DE); Oleg Krut, Hürth (DE); Martin Krönke, Cologne (DE)

(72) Inventors: Alexander Klimka, Cologne (DE); Oleg Krut, Hürth (DE); Martin Krönke, Cologne (DE)

( * ) Notice: Subject to any disclaimer, the term of this patent is extended or adjusted under 35 U.S.C. 154(b) by 0 days.

(21) Appl. No.: 16/486,937

(22) PCT Filed: Feb. 16, 2018

(86) PCT No.: PCT/EP2018/053862
§ 371 (c)(1),
(2) Date: Aug. 19, 2019

(87) PCT Pub. No.: WO2018/149956
PCT Pub. Date: Aug. 23, 2018

(65) Prior Publication Data
US 2020/0113992 A1 Apr. 16, 2020

(30) Foreign Application Priority Data
Feb. 17, 2017 (EP) .................................... 17156750

(51) Int. Cl.
A61K 39/085 (2006.01)
A61P 31/04 (2006.01)
C07K 14/31 (2006.01)
C07K 16/12 (2006.01)

(52) U.S. Cl.
CPC ............ *A61K 39/085* (2013.01); *A61P 31/04* (2018.01); *C07K 14/31* (2013.01); *C07K 16/1271* (2013.01); *C07K 2317/565* (2013.01)

(58) Field of Classification Search
CPC ....... A61K 39/085; A61P 31/04; C07K 14/31; C07K 16/1271; C07K 2317/565
See application file for complete search history.

(56) References Cited

FOREIGN PATENT DOCUMENTS

EP 1 987 836 A1 11/2008

OTHER PUBLICATIONS

Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS vol. 109 No. 31, pp. 12272-12273).*
Ellis (Vaccines, W.B. Saunders Company, Chapter 29, 1988, pp. 568-574).*
Boslego et al (Vaccines and Immunotherapy, 1991, Chapter 17).*
Sela-Culang et al. (Frontiers in Immunology, 2013 vol. 4, article 302, pp. 1-13).*
Glowalla, Eva et al., "Proteomics-Based Identification of Anchorless Cell Wall Proteins as Vaccine Candidates against *Staphylococcus aureus*." Infection and Immunity, vol. 77(7), Jul. 2009, pp. 2719-2729.
Yang, Hui-Jie et al., "Immunisation With Immunodominant Linear B Cell Epitopes Vaccine of Manganese Transport Protein C Confers Protection against *Staphylococcus aureus* Infection." PLOS ONE, vol. 11(2), Feb. 19, 2016, p. 1-16.

* cited by examiner

*Primary Examiner* — Robert A Zeman
(74) *Attorney, Agent, or Firm* — SALIWANCHIK, LLOYD & EISENSCHENK

(57) ABSTRACT

The present invention relates to pharmaceutical preparations for the treatment or the prevention of a Staphylococcal infection. They contain at least one polypeptide epitope, wherein said at least one polypeptide epitope induces protective antibodies in a patient in need thereof. The polypeptide epitopes according to the present invention can preferably be used for the preparation of a vaccine against a Staphylococcal infection, such as *Staphylococcus aureus*, including *Staphylococcus aureus* (MRSA). The present invention further relates to monoclonal antibodies capable of recognizing and binding to a polypeptide epitope according to the present invention, and the invention also relates to the use of the monoclonal antibodies for diagnosis and the prevention or therapy of Staphylococcal infection, including MRSA.

6 Claims, 38 Drawing Sheets
Specification includes a Sequence Listing.

Figure 1
A
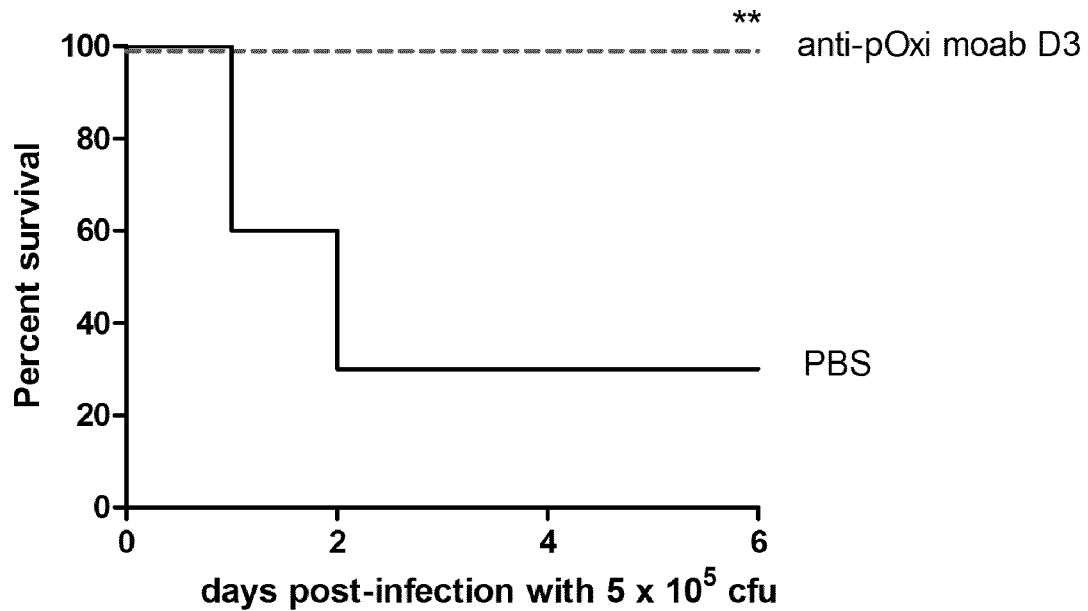
B
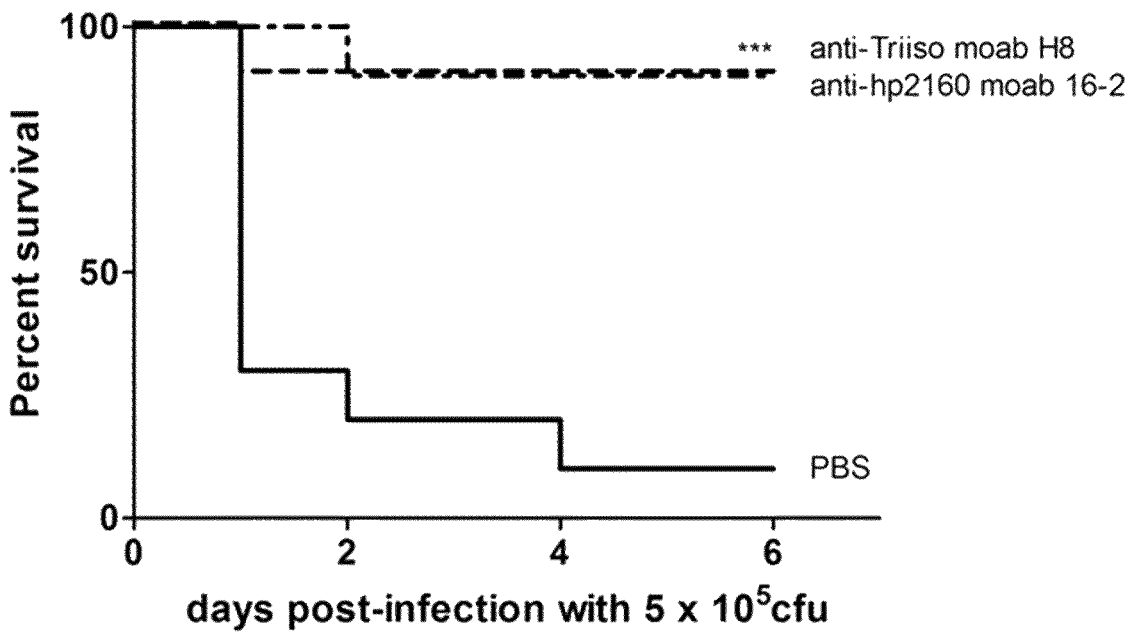

Figure 2
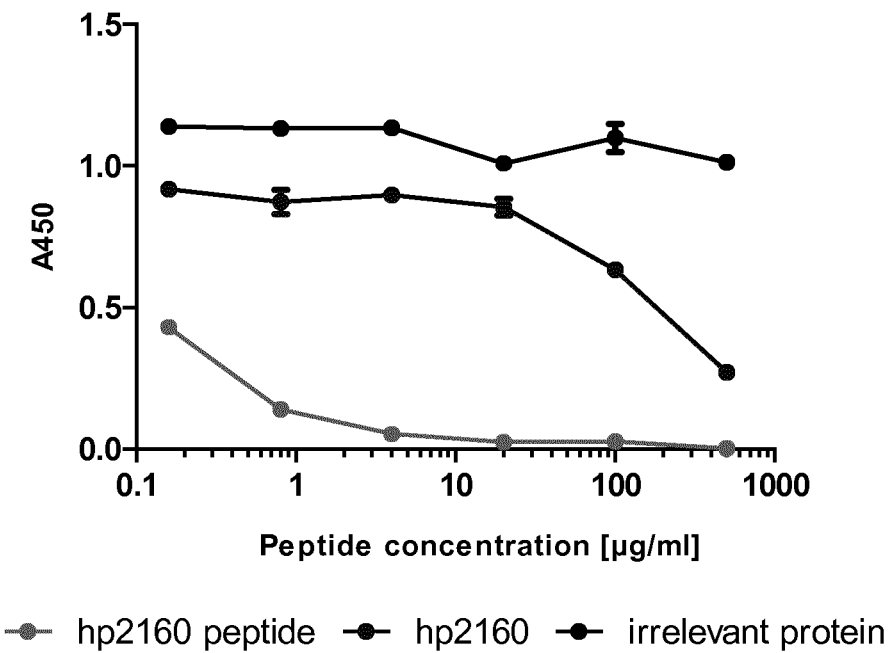
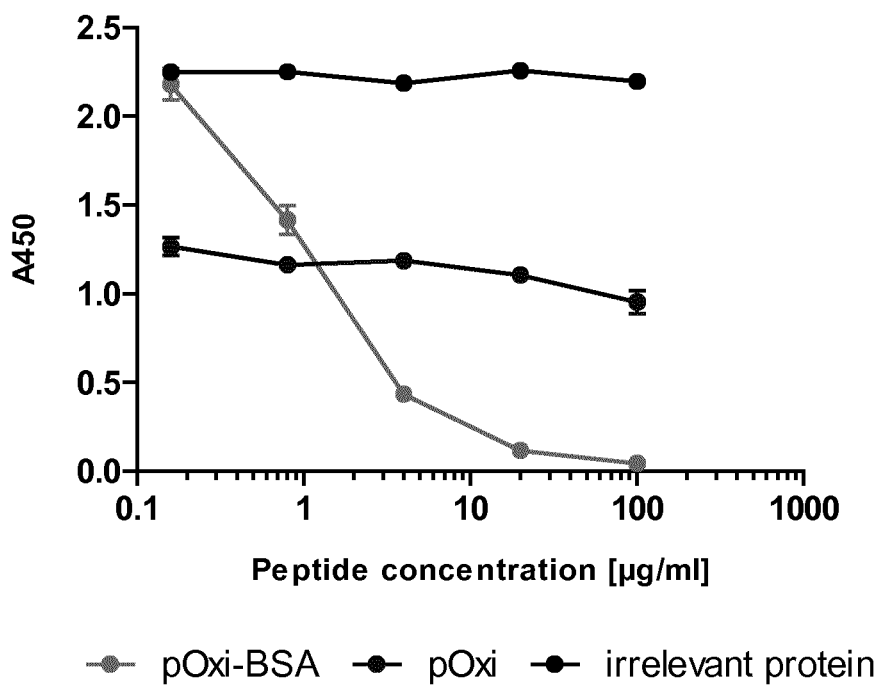

Figure 19
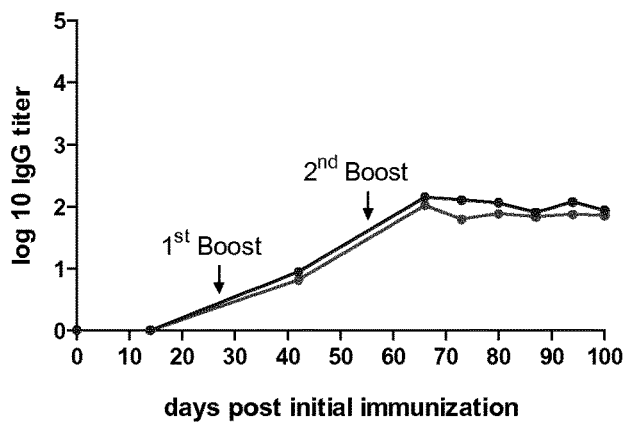
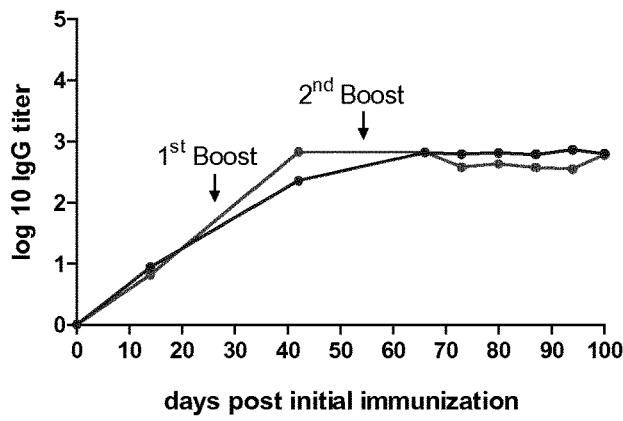
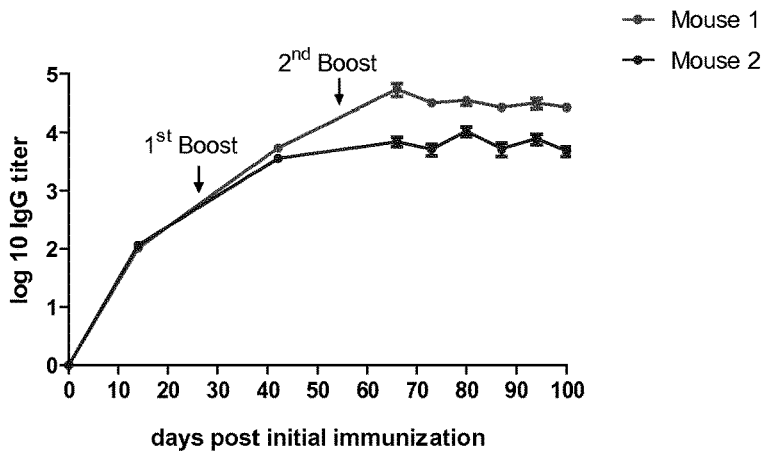

Cognate, linear epitope of anti-hp2160 moab 16-2

MIRNRVMNSVVNKYLLHNRSIMF<u>KNDQDVERFFYK</u>REIENRKKHKQPSTLN
VKANLEKLSLDDMQVFRFNFRHQIDKKILYIHGGFNALQPSPFHWRLLDKITLSTLYE
VVLPIYPKTPEFHIDDTFQAIQRVYDQLVSEVGHQNVVVMGDGSGGALALSFVQSLL
DNQQPLPNKLYLISPILDATLSNKDISDALIEQDAVLSQFGVNEIMKKWANGLPLTDK
RISPINGTIEGLPPVYMFGGGREMTHPDMKLFEQMMLQHHQYIEFYDYPKMVHDFP
IYPIRQSHKAIKQIAKSIDEDVTQNN

```
                          SEQUENCE LISTING

<160> NUMBER OF SEQ ID NOS: 32

<210> SEQ ID NO 1
<211> LENGTH: 466
<212> TYPE: PRT
<213> ORGANISM: Staphylococcus aureus

<400> SEQUENCE: 1

Met Thr Lys Ser Val Ala Ile Ile Gly Ala Gly Ile Thr Gly Leu Ser
1               5                   10                  15

Ser Ala Tyr Phe Leu Lys Gln Gln Asp Pro Asn Ile Asp Val Thr Ile
            20                  25                  30

Phe Glu Ala Ser Asn Arg Pro Gly Lys Ile Gln Ser Tyr Arg Lys
        35                  40                  45

Asp Gly Tyr Met Ile Glu Leu Gly Pro Glu Ser Tyr Leu Gly Arg Lys
    50                  55                  60

Thr Ile Met Thr Glu Leu Ala Lys Asp Ile Gly Leu Glu Gln Asp Ile
65                  70                  75                  80

Val Thr Asn Thr Gly Gln Ser Tyr Ile Phe Ala Lys Asn Lys Leu
                85                  90                  95

Tyr Pro Ile Pro Gly Gly Ser Ile Met Gly Ile Pro Thr Asp Ile Lys
            100                 105                 110

Pro Phe Val Thr Thr Lys Leu Ile Ser Pro Leu Gly Lys Leu Arg Ala
            115                 120                 125

Gly Leu Asp Leu Ile Lys Lys Pro Ile Gln Met Gln Asp Gly Asp Ile
    130                 135                 140

Ser Val Gly Ala Phe Phe Arg Ala Arg Leu Gly Asn Glu Val Leu Glu
145                 150                 155                 160

Asn Leu Ile Glu Pro Leu Met Gly Gly Ile Tyr Gly Thr Asp Ile Asp
                165                 170                 175

Lys Leu Ser Leu Met Ser Thr Phe Pro Asn Phe Lys Glu Lys Glu Glu
            180                 185                 190

Ala Phe Gly Ser Leu Ile Lys Gly Met Lys Asp Glu Lys Asn Lys Arg
        195                 200                 205

Leu Lys Gln Arg Gln Leu Tyr Pro Gly Ala Pro Lys Gly Gln Phe Lys
    210                 215                 220

Gln Phe Lys His Gly Leu Ser Ser Phe Ile Glu Ala Leu Glu Gln Asp
225                 230                 235                 240

Val Lys Asn Lys Gly Val Thr Ile Arg Tyr Asn Thr Ser Val Asp Asp
                245                 250                 255

Ile Ile Thr Ser Gln Lys Gln Tyr Lys Ile Val Tyr Ser Asn Gln Gln
            260                 265                 270

Glu Asp Val Phe Asp Gly Val Leu Val Thr Thr Pro His Gln Val Phe
        275                 280                 285

Leu Asn Trp Phe Gly Gln Asp Pro Ala Phe Asp Tyr Phe Lys Thr Met
    290                 295                 300

Asp Ser Thr Thr Val Ala Thr Val Leu Ala Phe Asp Glu Lys Asp
305                 310                 315                 320

Ile Glu Asn Thr Tyr Asp Gly Thr Gly Phe Val Ile Ala Arg Thr Ser
                325                 330                 335

Asp Thr Asp Ile Thr Ala Cys Thr Trp Thr Ser Lys Lys Trp Pro Phe
            340                 345                 350
```

Thr Thr Pro Glu Gly Lys Val Leu Ile Arg Ala Tyr Val Gly Lys Pro
        355                 360                 365

Gly Asp Thr Val Val Asp His Thr Asp Asn Glu Leu Val Ser Ile
    370                 375                 380

Val Arg Arg Asp Leu Ser Gln Met Met Thr Phe Lys Gly Asp Pro Glu
385                 390                 395                 400

Phe Thr Ile Val Asn Arg Leu Pro Lys Ser Met Pro Gln Tyr His Val
                405                 410                 415

Gly His Ile Gln Gln Ile Arg Gln Ile Gln Ala His Ile Lys Gln Thr
                420                 425                 430

Tyr Pro Arg Leu Arg Val Thr Gly Ala Ser Phe Glu Ala Val Gly Leu
                435                 440                 445

Pro Asp Cys Ile Thr Gln Gly Lys Val Ala Ala Glu Glu Val Ile Ala
                450                 455                 460

Glu Leu
465

<210> SEQ ID NO 2
<211> LENGTH: 253
<212> TYPE: PRT
<213> ORGANISM: Staphylococcus aureus

<400> SEQUENCE: 2

Met Arg Thr Pro Ile Ile Ala Gly Asn Trp Lys Met Asn Lys Thr Val
1               5                   10                  15

Gln Glu Ala Lys Asp Phe Val Asn Ala Leu Pro Thr Leu Pro Asp Ser
                20                  25                  30

Lys Glu Val Glu Ser Val Ile Cys Ala Pro Ala Ile Gln Leu Asp Ala
                35                  40                  45

Leu Thr Thr Ala Val Lys Glu Gly Lys Ala Gln Gly Leu Glu Ile Gly
            50                  55                  60

Ala Gln Asn Thr Tyr Phe Glu Asp Asn Gly Ala Phe Thr Gly Glu Thr
65              70                  75                  80

Ser Pro Val Ala Leu Ala Asp Leu Gly Val Lys Tyr Val Val Ile Gly
                85                  90                  95

His Ser Glu Arg Arg Glu Leu Phe His Glu Thr Asp Glu Glu Ile Asn
                100                 105                 110

Lys Lys Ala His Ala Ile Phe Lys His Gly Met Thr Pro Ile Ile Cys
                115                 120                 125

Val Gly Glu Thr Asp Glu Glu Arg Glu Ser Gly Lys Ala Asn Asp Val
                130                 135                 140

Val Gly Glu Gln Val Lys Lys Ala Val Ala Gly Leu Ser Glu Asp Gln
145                 150                 155                 160

Leu Lys Ser Val Val Ile Ala Tyr Glu Pro Ile Trp Ala Ile Gly Thr
                165                 170                 175

Gly Lys Ser Ser Thr Ser Glu Asp Ala Asn Glu Met Cys Ala Phe Val
                180                 185                 190

Arg Gln Thr Ile Ala Asp Leu Ser Ser Lys Glu Val Ser Glu Ala Thr
                195                 200                 205

Arg Ile Gln Tyr Gly Gly Ser Val Lys Pro Asn Asn Ile Lys Glu Tyr
                210                 215                 220

Met Ala Gln Thr Asp Ile Asp Gly Ala Leu Val Gly Gly Ala Ser Leu
225                 230                 235                 240

Lys Val Glu Asp Phe Val Gln Leu Leu Glu Gly Ala Lys
                245                 250

<210> SEQ ID NO 3
<211> LENGTH: 306
<212> TYPE: PRT
<213> ORGANISM: Staphylococcus aureus

<400> SEQUENCE: 3

Met Ile Arg Asn Arg Val Met Asn Ser Val Asn Lys Tyr Leu Leu
1               5                   10                  15

His Asn Arg Ser Ile Met Phe Lys Asn Asp Gln Asp Val Glu Arg Phe
            20                  25                  30

Phe Tyr Lys Arg Glu Ile Glu Asn Arg Lys His Lys Gln Pro Ser
        35                  40                  45

Thr Leu Asn Val Lys Ala Asn Leu Glu Lys Leu Ser Leu Asp Asp Met
50                  55                  60

Gln Val Phe Arg Phe Asn Phe Arg His Gln Ile Asp Lys Lys Ile Leu
65                  70                  75                  80

Tyr Ile His Gly Gly Phe Asn Ala Leu Gln Pro Ser Pro Phe His Trp
                85                  90                  95

Arg Leu Leu Asp Lys Ile Thr Leu Ser Thr Leu Tyr Glu Val Val Leu
            100                 105                 110

Pro Ile Tyr Pro Lys Thr Pro Glu Phe His Ile Asp Asp Thr Phe Gln
        115                 120                 125

Ala Ile Gln Arg Val Tyr Asp Gln Leu Val Ser Glu Val Gly His Gln
    130                 135                 140

Asn Val Val Val Met Gly Asp Gly Ser Gly Ala Leu Ala Leu Ser
145                 150                 155                 160

Phe Val Gln Ser Leu Leu Asp Asn Gln Gln Pro Leu Pro Asn Lys Leu
                165                 170                 175

Tyr Leu Ile Ser Pro Ile Leu Asp Ala Thr Leu Ser Asn Lys Asp Ile
            180                 185                 190

Ser Asp Ala Leu Ile Glu Gln Asp Ala Val Leu Ser Gln Phe Gly Val
        195                 200                 205

Asn Glu Ile Met Lys Lys Trp Ala Asn Gly Leu Pro Leu Thr Asp Lys
210                 215                 220

Arg Ile Ser Pro Ile Asn Gly Thr Ile Glu Gly Leu Pro Pro Val Tyr
225                 230                 235                 240

Met Phe Gly Gly Gly Arg Glu Met Thr His Pro Asp Met Lys Leu Phe
                245                 250                 255

Glu Gln Met Met Leu Gln His His Gln Tyr Ile Glu Phe Tyr Asp Tyr
            260                 265                 270

Pro Lys Met Val His Asp Phe Pro Ile Tyr Pro Ile Arg Gln Ser His
        275                 280                 285

Lys Ala Ile Lys Gln Ile Ala Lys Ser Ile Asp Glu Asp Val Thr Gln
    290                 295                 300

Asn Asn
305

<210> SEQ ID NO 4
<211> LENGTH: 12
<212> TYPE: PRT
<213> ORGANISM: Staphylococcus aureus

<400> SEQUENCE: 4

Lys Asn Asp Gln Asp Val Glu Arg Phe Phe Tyr Lys
1               5                   10

<210> SEQ ID NO 5
<211> LENGTH: 16
<212> TYPE: PRT
<213> ORGANISM: Staphylococcus aureus

<400> SEQUENCE: 5

His Thr Asp Asn Glu Leu Val Ser Ile Val Arg Arg Asp Leu Ser Gln
1               5                   10                  15

<210> SEQ ID NO 6
<211> LENGTH: 108
<212> TYPE: PRT
<213> ORGANISM: Staphylococcus aureus

<400> SEQUENCE: 6

Asn Lys Lys Ala His Ala Ile Phe Lys His Gly Met Thr Pro Ile Ile
1               5                   10                  15

Cys Val Gly Glu Thr Asp Glu Glu Arg Glu Ser Gly Lys Ala Asn Asp
                20                  25                  30

Val Val Gly Glu Gln Val Lys Lys Ala Val Ala Gly Leu Ser Glu Asp
            35                  40                  45

Gln Leu Lys Ser Val Val Ile Ala Tyr Glu Pro Ile Trp Ala Ile Gly
        50                  55                  60

Thr Gly Lys Ser Ser Thr Ser Glu Asp Ala Asn Glu Met Cys Ala Phe
65                  70                  75                  80

Val Arg Gln Thr Ile Ala Asp Leu Ser Ser Lys Glu Val Ser Glu Ala
                85                  90                  95

Thr Arg Ile Gln Tyr Gly Gly Ser Val Lys Pro Asn
            100                 105

<210> SEQ ID NO 7
<211> LENGTH: 15
<212> TYPE: PRT
<213> ORGANISM: Staphylococcus aureus

<400> SEQUENCE: 7

Asn Lys Lys Ala His Ala Ile Phe Lys His Gly Met Thr Pro Ile
1               5                   10                  15

<210> SEQ ID NO 8
<211> LENGTH: 11
<212> TYPE: PRT
<213> ORGANISM: Staphylococcus aureus

<400> SEQUENCE: 8

Gln Leu Lys Ser Val Val Ile Ala Tyr Glu Pro
1               5                   10

<210> SEQ ID NO 9
<211> LENGTH: 15
<212> TYPE: PRT
<213> ORGANISM: Staphylococcus aureus

<400> SEQUENCE: 9

Ala Asn Glu Met Cys Ala Phe Val Arg Gln Thr Ile Ala Asp Leu
1               5                   10                  15

<210> SEQ ID NO 10
<211> LENGTH: 20
<212> TYPE: PRT
<213> ORGANISM: Staphylococcus aureus -continued

```
<400> SEQUENCE: 10

Ser Ser Lys Glu Val Ser Glu Ala Thr Arg Ile Gln Tyr Gly Gly Ser
1               5                   10                  15

Val Lys Pro Asn
            20

<210> SEQ ID NO 11
<211> LENGTH: 130
<212> TYPE: PRT
<213> ORGANISM: artificial sequence
<220> FEATURE:
<223> OTHER INFORMATION: triepitope peptide sequence

<400> SEQUENCE: 11

Thr Asp Asn Glu Leu Val Ser Ile Val Arg Arg Asp Lys Ala His Ala
1               5                   10                  15

Ile Phe Lys His Gly Met Thr Pro Ile Ile Cys Val Gly Glu Thr Asp
                20                  25                  30

Glu Glu Arg Glu Ser Gly Lys Ala Asn Asp Val Val Gly Glu Gln Val
            35                  40                  45

Lys Lys Ala Val Ala Gly Leu Ser Glu Asp Gln Leu Lys Ser Val Val
        50                  55                  60

Ile Ala Tyr Glu Pro Ile Trp Ala Ile Gly Thr Gly Lys Ser Ser Thr
65                  70                  75                  80

Ser Glu Asp Ala Asn Glu Met Cys Ala Phe Val Arg Gln Thr Ile Ala
                85                  90                  95

Asp Leu Ser Ser Lys Glu Val Ser Glu Ala Thr Arg Ile Gln Tyr Gly
            100                 105                 110

Gly Ser Val Lys Pro Asn Lys Asn Asp Gln Asp Val Glu Arg Phe Phe
        115                 120                 125

Tyr Lys
    130

<210> SEQ ID NO 12
<211> LENGTH: 118
<212> TYPE: PRT
<213> ORGANISM: artificial sequence
<220> FEATURE:
<223> OTHER INFORMATION: diepitope peptide sequence

<400> SEQUENCE: 12

Thr Asp Asn Glu Leu Val Ser Ile Val Arg Arg Asp Lys Ala His Ala
1               5                   10                  15

Ile Phe Lys His Gly Met Thr Pro Ile Ile Cys Val Gly Glu Thr Asp
                20                  25                  30

Glu Glu Arg Glu Ser Gly Lys Ala Asn Asp Val Val Gly Glu Gln Val
            35                  40                  45

Lys Lys Ala Val Ala Gly Leu Ser Glu Asp Gln Leu Lys Ser Val Val
        50                  55                  60

Ile Ala Tyr Glu Pro Ile Trp Ala Ile Gly Thr Gly Lys Ser Ser Thr
65                  70                  75                  80

Ser Glu Asp Ala Asn Glu Met Cys Ala Phe Val Arg Gln Thr Ile Ala
                85                  90                  95

Asp Leu Ser Ser Lys Glu Val Ser Glu Ala Thr Arg Ile Gln Tyr Gly
            100                 105                 110

Gly Ser Val Lys Pro Asn
        115
```

<210> SEQ ID NO 13
<211> LENGTH: 130
<212> TYPE: PRT
<213> ORGANISM: artificial sequence
<220> FEATURE:
<223> OTHER INFORMATION: diepitope peptide sequence

<400> SEQUENCE: 13

Thr Asp Asn Glu Leu Val Ser Ile Val Arg Arg Asp Lys Ala His Ala
1               5                   10                  15

Ile Phe Lys His Gly Met Thr Pro Ile Ile Cys Val Gly Glu Thr Asp
            20                  25                  30

Glu Glu Arg Glu Ser Gly Lys Ala Asn Asp Val Val Gly Glu Gln Val
        35                  40                  45

Lys Lys Ala Val Ala Gly Leu Ser Glu Asp Gln Leu Lys Ser Val Val
    50                  55                  60

Ile Ala Tyr Glu Pro Ile Trp Ala Ile Gly Thr Gly Lys Ser Ser Thr
65                  70                  75                  80

Ser Glu Asp Ala Asn Glu Met Cys Ala Phe Val Arg Gln Thr Ile Ala
                85                  90                  95

Asp Leu Ser Ser Lys Glu Val Ser Glu Ala Thr Arg Ile Gln Tyr Gly
            100                 105                 110

Gly Ser Val Lys Pro Asn Thr Asp Asn Glu Leu Val Ser Ile Val Arg
        115                 120                 125

Arg Asp
    130

<210> SEQ ID NO 14
<211> LENGTH: 118
<212> TYPE: PRT
<213> ORGANISM: artificial sequence
<220> FEATURE:
<223> OTHER INFORMATION: diepitope peptide sequence

<400> SEQUENCE: 14

Lys Ala His Ala Ile Phe Lys His Gly Met Thr Pro Ile Ile Cys Val
1               5                   10                  15

Gly Glu Thr Asp Glu Glu Arg Glu Ser Gly Lys Ala Asn Asp Val Val
            20                  25                  30

Gly Glu Gln Val Lys Lys Ala Val Ala Gly Leu Ser Glu Asp Gln Leu
        35                  40                  45

Lys Ser Val Val Ile Ala Tyr Glu Pro Ile Trp Ala Ile Gly Thr Gly
    50                  55                  60

Lys Ser Ser Thr Ser Glu Asp Ala Asn Glu Met Cys Ala Phe Val Arg
65                  70                  75                  80

Gln Thr Ile Ala Asp Leu Ser Ser Lys Glu Val Ser Glu Ala Thr Arg
                85                  90                  95

Ile Gln Tyr Gly Gly Ser Val Lys Pro Asn Thr Asp Asn Glu Leu Val
            100                 105                 110

Ser Ile Val Arg Arg Asp
        115

<210> SEQ ID NO 15
<211> LENGTH: 10
<212> TYPE: PRT
<213> ORGANISM: Mus musculus

<400> SEQUENCE: 15

Gly Tyr Thr Phe Thr Asp Tyr Ser Met His
1               5                   10

<210> SEQ ID NO 16
<211> LENGTH: 17
<212> TYPE: PRT
<213> ORGANISM: Mus musculus

<400> SEQUENCE: 16

Trp Ile Asp Thr Glu Thr Gly Glu Pro Thr Phe Ala Asp Asp Phe Lys
1               5                   10                  15

Gly

<210> SEQ ID NO 17
<211> LENGTH: 11
<212> TYPE: PRT
<213> ORGANISM: Mus musculus

<400> SEQUENCE: 17

Pro Leu Leu Arg Leu Ser Phe Ala Met Asp Ser
1               5                   10

<210> SEQ ID NO 18
<211> LENGTH: 15
<212> TYPE: PRT
<213> ORGANISM: Mus musculus

<400> SEQUENCE: 18

Ser Ala Ser Glu Asn Leu Asp Ile Tyr Gly Asn Ser Phe Met His
1               5                   10                  15

<210> SEQ ID NO 19
<211> LENGTH: 7
<212> TYPE: PRT
<213> ORGANISM: Mus musculus

<400> SEQUENCE: 19

Arg Ala Ser Lys Leu Glu Ser
1               5

<210> SEQ ID NO 20
<211> LENGTH: 9
<212> TYPE: PRT
<213> ORGANISM: Mus musculus

<400> SEQUENCE: 20

Gln Gln Thr Ser Glu Asp Pro Arg Thr
1               5

<210> SEQ ID NO 21
<211> LENGTH: 6
<212> TYPE: PRT
<213> ORGANISM: Mus musculus

<400> SEQUENCE: 21

Ser Arg Tyr Trp Ile Glu
1               5

<210> SEQ ID NO 22
<211> LENGTH: 17
<212> TYPE: PRT
<213> ORGANISM: Mus musculus -continued

```
<400> SEQUENCE: 22

Glu Ile Leu Pro Gly Ser Gly Ser Thr Asn Tyr Asn Glu Lys Phe Lys
1               5                   10                  15

Gly

<210> SEQ ID NO 23
<211> LENGTH: 12
<212> TYPE: PRT
<213> ORGANISM: Mus musculus

<400> SEQUENCE: 23

Phe Tyr Ser Gly Asn Phe Val Gly Pro Val Asp Tyr
1               5                   10

<210> SEQ ID NO 24
<211> LENGTH: 16
<212> TYPE: PRT
<213> ORGANISM: Mus musculus

<400> SEQUENCE: 24

Lys Ser Ser Gln Ser Leu Ser Asp Ser Asp Gly Lys Thr Tyr Leu Asn
1               5                   10                  15

<210> SEQ ID NO 25
<211> LENGTH: 7
<212> TYPE: PRT
<213> ORGANISM: Mus musculus

<400> SEQUENCE: 25

Leu Val Ser Lys Val Asp Ser
1               5

<210> SEQ ID NO 26
<211> LENGTH: 9
<212> TYPE: PRT
<213> ORGANISM: Mus musculus

<400> SEQUENCE: 26

Trp Gln Gly Thr His Phe Pro Phe Thr
1               5

<210> SEQ ID NO 27
<211> LENGTH: 10
<212> TYPE: PRT
<213> ORGANISM: Mus musculus

<400> SEQUENCE: 27

Gly Phe Thr Phe Ser Ala Tyr Trp Met Asn
1               5                   10

<210> SEQ ID NO 28
<211> LENGTH: 19
<212> TYPE: PRT
<213> ORGANISM: Mus musculus

<400> SEQUENCE: 28

Glu Ile Arg Met Lys Ser Asn Asn Tyr Ala Thr His Tyr Ala Glu Ser
1               5                   10                  15

Val Lys Gly

<210> SEQ ID NO 29
<211> LENGTH: 7
```

```
<212> TYPE: PRT
<213> ORGANISM: Mus musculus

<400> SEQUENCE: 29

Tyr Lys Tyr Asp Gly Ala Tyr
1               5

<210> SEQ ID NO 30
<211> LENGTH: 10
<212> TYPE: PRT
<213> ORGANISM: Mus musculus

<400> SEQUENCE: 30

Ser Ala Ser Ser Thr Val Asn Tyr Met His
1               5                   10

<210> SEQ ID NO 31
<211> LENGTH: 7
<212> TYPE: PRT
<213> ORGANISM: Mus musculus

<400> SEQUENCE: 31

Asp Thr Ser Lys Leu Ala Ser
1               5

<210> SEQ ID NO 32
<211> LENGTH: 8
<212> TYPE: PRT
<213> ORGANISM: Mus musculus

<400> SEQUENCE: 32

His Gln Arg Ser Ser Tyr Pro Thr
1               5
```

POLYPEPTIDE EPITOPES OF S. AUREUS AND RESPECTIVE MONOCLONAL ANTIBODIES FOR THE TREATMENT OF INFECTIONS AND IMMUNE-DIAGNOSIS

CROSS REFERENCE TO RELATED APPLICATIONS

This application is a National Stage Application of International Application Number PCT/EP2018/053862, filed Feb. 16, 2018; which claims priority to European Patent Application No. 17156750.6, filed Feb. 17, 2017.

The Sequence Listing for this application is labeled "SeqList-16Aug19-ST25.txt", which was created on Aug. 16, 2019 and is 19 KB. The entire content is incorporated herein by reference in its entirety.

The present invention relates to pharmaceutical preparations for the treatment or the prevention of a Staphylococal infection. They contain at least one polypeptide epitope, wherein said at least one polypeptide epitope induces protective antibodies in a patient in need thereof. The polypeptide epitopes according to the present invention can preferably be used for the preparation of a vaccine against a Staphylococal infection, such as caused by *Staphylococcus aureus*, including Methicillin-resistant *Staphylococcus aureus* (MRSA). The present invention further relates to monoclonal antibodies capable of recognizing and binding to a polypeptide epitope according to the present invention, and the invention also relates to the use of the monoclonal antibodies for diagnosis and the prevention or therapy of Staphylococcal infection, including such caused by MRSA.

BACKGROUND OF THE PRESENT INVENTION

Infections caused by *Staphylococcus aureus* are a major concern cause for clinicians. Besides resistance to beta-lactams, hospital MRSA strains present resistance to most other available antimicrobial classes, with the use of glycopeptides (vancomycin and teicoplanin) remaining as first choice treatment. However, the growing isolation of MRSA strains in communities in the United States and Australia, together with the identification of MRSA strains with intermediate resistance to vancomycin in Japan, the United States, and Brazil are cause for concerns. MRSA represents a strong candidate for becoming the fearful "superbug", i.e. a pathogen resistant to all drugs available nowadays.

It is known that all gram-positive bacteria (also those belonging to the genus of *Staphylococcus*) contain in the cell wall several specific carbohydrates and proteins. In the course of the present invention several proteins have been identified that play a possible role in the dynamic equilibrium of the outer cell wall.

The humoral immune response is mediated by antibody molecules secreted by plasma cells. Antigen that binds to the B-cell antigen receptor signals B-cells and is at the same time internalized and processed into peptides that activate armed helper T-cells. Signals from the bound antigen and from the helper T-cell induce the B-cell to proliferate and differentiate into plasma cells secreting specific antibody. These antibodies protect the host from infection in three main ways. First, said antibodies can inhibit the toxic effects or infectivity of pathogens by binding to them. Such antibodies are termed neutralizing antibodies. Second, by coating the pathogens, said antibodies can enable accessory cells that recognize the Fc portions of arrays of antibodies to ingest and kill the pathogen. This process is called opsonisation. Third, antibodies can trigger the activation of the complement system. Complement proteins can strongly enhance opsonisation or can directly kill certain bacterial cells.

However, it is known that, in hospital infections, patients can be immunodepressed. In these cases, a vaccine would not always be able to generate protective antibodies in due time to control a bacterial infection. Therefore, at least those patients may be treated by the infusion of the prepared protective antibodies, including monoclonal antibodies.

Mastitis is the leading cause of economic losses in dairy cattle herds, because of poor yields in the infected udder, veterinary treatments, milk that must be discarded (contaminated with pathogens and/or with antibiotic residues), and anticipated culling. As for prevalence, *S. aureus* is one of the three most important mastitis pathogens, alongside *Escherichia coli* and *Streptococcus uberis*. This is true in all the milk producing countries, and even in those which have implemented strict mastitis control programmes. The average annual cost of mastitis in a herd of 100 dairy cows is estimated to be €4896 (Halasa T, Osterås O, Hogeveen H, van Werven T, Nielen M. Meta-analysis of dry cow management for dairy cattle. Part 1. Protection against new intramammary infections. J Dairy Sci. 2009 July; 92(7): 3134-49). High prevalence in a dairy herd can be a threat to the sustainability of the livestock.

EP 1987836 relates to a pharmaceutical composition or a medicament, notably a protective *Staphylococcus aureus* vaccine, comprising at least one cell wall-associated *S. aureus* protein or a fragment or derivative thereof causing an immune response that induces opsonophagocytic activity of human neutrophils for *S. aureus*. The invention further provides particular cell wall-associated *S. aureus* proteins and their use.

Anchorless cell wall proteins from *S. aureus* ATCC 29213 were identified as vaccine candidates by subtractive proteome and MALDI-TOF analysis (Glowalla et al., "Proteomics-Based Identification of Anchorless Cell Wall Proteins as Vaccine Candidates against *Staphylococcus aureus*", Inf. Immun. vol. 77, no. 7, 1 Jul. 2009, pages 2719-27292009). Some of them, for example protoporphyrinogen oxidase (pOxi), triosephosphate isomerase (Triiso) and the hypothetical protein 2160 (hp2160), when used as full-length vaccines, achieved a repetitive protection in an established murine sepsis model. The rhp2160 protein does contain the epitope of SEQ ID NO:4 according to the present invention.

For the production of vaccines it is important that the antigen elicits antibodies which inhibit the pathogenic activity of the pathogenic microorganism. However, only few antigens have been identified so far that may offer the potential of inducing a protective immune response, and therefore would be promising vaccine targets.

It is therefore an object of the present invention to provide new epitope sequences (antigens) that can be used in order to produce protective antibodies, preferably IgG antibodies, against said epitope sequences. It is furthermore an object of the present invention, to provide vaccine compositions against Staphylococci, in particular *S. aureus*, including MRSA, based on said epitope sequences. It is furthermore an object of the present invention to provide new and effective antibodies as diagnostics and therapeutics against Staphylococci, in particular *S. aureus*, including MRSA, based on the epitope sequences. Other objects and advantages of the present invention will become apparent to the person of skill when studying the following description.

In a first aspect of the present invention, a pharmaceutical composition for the treatment or the prevention of a Staphylococcal infection is provided which is characterized in that it comprises at least one polypeptide epitope sequence selected from the group of SEQ ID NO: 4 to SEQ ID NO: 14, wherein said at least one polypeptide epitope sequence induces protective antibodies in a patient in need thereof. *Staphylococcus* in the context of the present application shall mean *Staphylococcus* species (Staphylococci), preferably *Staphylococcus aureus*, preferably *Staphylococcus aureus* (MRSA).

The present invention provides epitopes that are not immunodominant and thus could not have been identified using the technology of the state of the art in the field. Here, the epitopes (e.g. discontinuous ones) were identified using solely protective antibodies.

In the context of the present invention, intravenous immunoglobulin preparations (IVIG) were used that contain a broad spectrum of opsonising antibodies against various pathogens including *S. aureus*. Employing 2-DE gel electrophoresis, subtractive immunoblotting and mass spectrometry several cell wall-associated proteins were identified as novel potential vaccine protein targets. This method for the identification of potential vaccines is called SUPRA (subtractive proteome analysis). Three of them, protoporphyrinogen oxidase (pOxi), triosephosphate isomerase (Triiso) and the hypothetical protein 2160 (hp2160), when used as full-length vaccines, achieved a repetitive protection in an established murine sepsis model. Using array technology, specific epitopes were identified (SEQ ID NO: 4 to SEQ ID NO: 6) that were recognized by protective antibodies and were either linear (anti-hp2160 moAb 16-2, anti-pOxi moAb D3) or discontinuous (anti-Triiso moAb H8). Both epitopes and antibodies thus constitute preferred embodiments of the invention.

It could also be shown that non-protective antibodies do not compete with protective antibodies for a binding to the antigen, e.g. hp2160 (FIG. 30), Triiso (FIG. 33), and pOxi (FIG. 36), indicating a specific binding site.

In the context of the present invention, an "epitope" is defined as an amino acid sequence of usually between 6 and 15 residues (linear) or of a combination of such amino acid sequences as a discontinuous epitope (i.e. one in which amino acids are in close proximity in the folded protein, but distant when unfolded) as part of a longer amino acid sequence, as herein exemplified by loops of AA 1-15 (NK-KAHAIFKHGMTPI, SEQ ID NO: 7), 49-59 (QLKSVVI-AYEP, SEQ ID NO: 8), 74-88 (ANEMCAFVRQTIADL, SEQ ID NO: 9) and 89-108 (SSKEVSEAT-RIQYGGSVKPN, SEQ ID NO: 10) in a stretch of 108 amino acids in case of anti-Triiso moab H8, wherein said loops may contain up to three homologous amino acid substitutions, respectively. "Homologous" is defined as a substitution of one (natural) amino acid by another one having a non-negative value in a Blosum62 (Henikoff et al PNAS, 1992, 89(22):10915-9) matrix, and wherein said at least one polypeptide epitope sequence induces protective antibodies in a patient in need thereof.

In the context of the present invention, a "patient" shall mean both a human or animal patient, in particular mammalian patients. Particularly preferred patients are humans and lifestock, e.g. cattle or swine (see, for example, Peton V, Le Loir Y. *Staphylococcus aureus* in veterinary medicine. Infect Genet Evol. 2014 January; 21:602-15. Epub 2013 Aug. 23).

Preferred is the pharmaceutical composition according to the present invention, wherein said polypeptide epitope sequence is selected from a continuous or discontinuous epitope. It was surprisingly found that the protective epitope for the protein Triiso was a discontinuous one (see examples).

Further preferred is the pharmaceutical composition according to the present invention, wherein said polypeptide epitope sequence is covalently bound to an immunocarrier, in particular a protein, a carbohydrate, and/or a glycoconjugate. Further preferred is the pharmaceutical composition according to the present invention, comprising a branched epitope peptide (multiple antigenic peptide, MAP), usually using a lysine backbone to which up to 8 epitope peptides are attached, omitting the need for a carrier protein conjugation, if a helper T-cell epitope is incorporated or attached to the epitope peptide. Another subject of the invention is a pharmaceutical composition, especially a vaccine, comprising the epitope and/or polyepitope peptide as defined by the invention, useful for the immunization of a subject against an infection or the treatment of a subject having an infection, wherein the infection is preferably caused by MRSA. This pharmaceutical formulation of a medicament to be used as a vaccine is known to the person skilled in the art, and described in the respective literature. Usually, a solution of the epitope, possibly coupled to an immunocarrier is dissolved in a physiologically acceptable solution like a buffer. The solution must be stabilized in order to avoid an undesired precipitation of the immunologically active compounds. The vaccine is preferably produced in the form of a solution adapted to injection, preferably intramuscular injection. Other forms of pharmaceutical formulations like plasters or sprays are also acceptable provided the epitope(s) come(s) in sufficient contact with the immune system and the formation of specific antibodies is elicited.

Another aspect of the invention is the pharmaceutical composition according to the present invention, comprising (a) polypeptide epitope sequence(s) as a diepitope and/or triepitope sequence construct, in particular according to SEQ ID NO: 11 to SEQ ID NO: 14. These constructs (see below in the examples) have proven to be of particular and advantageous use in the context of the present invention, e.g. in the prevention and/or the treatment of bacterial infection, and in particular the production of antibodies as described herein.

Particularly preferred is the pharmaceutical composition according to the present invention, characterized in that said bacterial infection is caused by *Staphylococcus*, in particular MRSA.

Yet another aspect of the invention then relates to the pharmaceutical composition according to the present invention, characterized in that it comprises (b) at least one pharmaceutically acceptable adjuvant. Preferably, said pharmaceutical composition constitutes a vaccine. The vaccine is preferably produced in the form of a solution adapted to injection, preferably intramuscular injection. Other forms of pharmaceutical formulations like plasters or sprays are also acceptable provided the antigen comes in sufficient contact with the immune system and the formation of specific antibodies are elicited.

The vaccine comprises also a pharmaceutically acceptable adjuvant. The adjuvant promotes the protective IgG subtype antibodies. Typical adjuvants include but are not limited to complete Freund's adjuvant (CFA), incomplete Freund's adjuvant (IFA), alum and other adjuvants suitable for human use (e.g. virus-like particles). Polymers like dextran sulfate have been shown to be also a potent stimulator of IgG antibodies against bacterial cell surface antigen. Other adjuvants include incomplete adjuvants; salt i.e. AlK (SO$_4$)$_2$, AlNa(SO$_4$)$_2$, AlNH$_4$(SO$_4$)$_2$, solica, kaolin, carbon polynucleotide, i.e. poly IC and poly AU. Preferred adjuvants include QuilA, CpG-DNA and Alhydrogel.

The composition may further encompass substances increasing their capacity to stimulate T cells. These include T helper cell epitopes, lipids or liposomes or preferred modifications as described in WO 01/78767. Another way to increase the T cell stimulating capacity of epitopes is their formulation with immune stimulating substances for instance cytokines or chemokines like interleukin-2, -7, -12, -18, class I and II interferons (IFN), especially IFN-gamma, GM-CSF, TNF-alpha, flt3-ligand and others.

Yet another aspect of the invention then relates to at least one polypeptide epitope sequence selected from the group of SEQ ID NO: 4 to SEQ ID NO: 14, for use in medicine, in particular for the treatment or prevention of a bacterial infection, preferably wherein the infection is caused by *Staphylococcus*, in particular MRSA. Preferred is the at least one polypeptide epitope sequence for use according to the present invention, wherein said polypeptide or contiguous fragment thereof is covalently bound to an immunocarrier (e.g. KLH, ISCAR, cross-reacting material (CRM197) of diphtheria toxin, tetanus toxoid (T), meningococcal outer membrane protein complex (OMPC), diphtheria toxoid (D), *H. influenzae* protein D (HiD) see, for example, Pichichero M. E. Protein carriers of conjugate vaccines Characteristics, development, and clinical trials, Hum Vaccin Immunother. 2013 Dececember 1; 9(12): 2505-2523.) and as described herein.

Yet another aspect of the invention then relates to the use of at least one polypeptide epitope sequence selected from the group of SEQ ID NO: 4 to SEQ ID NO: 14 for the preparation of antibodies.

According to this embodiment, the invention also provides antibodies against the polypeptide epitope(s) as described above (said antibodies may be polyclonal or monoclonal). Such antibodies that can be used employed as a diagnostic, a pharmaceutical composition or medicament or the method as described can be prepared (i.e. raised against the epitope/antigen) by suitable methods known to a skilled person.

In contrast to commonly designed antibodies, e.g. the ones that were identified by merely testing linear, overlapping peptides as in Zhao et al. 2015 (Zhao Z, Sun H Q, Wei S S, Li B, Feng Q, Zhu J, Zeng H, Zou Q M, Wu C. Multiple B-cell epitope vaccine induces a *Staphylococcus* enterotoxin B-specific IgG1 protective response against MRSA infection. Sci Rep. 2015 Jul. 23; 5:12371) and which could be protective and non-protective, the present methodology consisting of a) generation of antibodies from the repertoire of animals that survived the *S. aureus* infection; b) testing the individual ABs for their protective capacity; and c) identification of the epitope for protective antibodies provides surprisingly protective antibodies. In the diagnostic context, the antibody may be linked to a suitable detection moiety (such as dye or enzyme), allowing the epitope/protein to be detected. Alternatively, it may also be linked to suitable carrier, such as beads, or a suitable solid surface (membrane or silicone).

According to another preferred aspect of the present invention, it is very beneficial to provide monoclonal or polyclonal antibody therapies which target antigenic polypeptides of *S. aureus* as described herein and have the potential to support a therapy of an infection or eliminate the pathogen and the disease altogether. Therefore, another subject of the invention relates to an antibody or functional active fragment thereof which binds specifically to the epitope sequences of the invention. In a preferred embodiment the antibody is a monoclonal, polyclonal, chimeric, bispecific, human and/or humanized antibody or functional active variant thereof, as well as an aptamer. The antibody or fragment thereof can be recombinantly produced. In another preferred embodiment the functional active fragment comprises a Fab fragment. Antibodies generated against the epitopes/antigens (polypeptides) of the present invention can be obtained by direct injection of the antigens, fragments or variants thereof into an animal or by administering the antigens, fragments or variants thereof to an animal, preferably a non-human. The antibody so obtained will then bind the epitope/antigens.

For the preparation of monoclonal antibodies, any technique known in the art, which provides antibodies produced by continuous cell line cultures, e.g. a hybridoma cell line, can be used. Techniques described for the production of single chain antibodies (e.g. U.S. Pat. No. 4,946,778) can be adapted to produce single chain antibodies to the epitopes according to this invention. Also, transgenic mice or other organisms such as other mammals may be used to express humanized antibodies to epitopes according to this invention. Still another subject of the invention relates to a hybridoma cell line which produces the antibody of the invention. Hybridoma cell lines expressing desirable monoclonal antibodies are generated by well-known conventional techniques. Similarly, desirable high titer antibodies are generated by applying known recombinant techniques to the monoclonal or polyclonal antibodies developed to these antigens (see, e.g., PCT Patent Application No. PCT/GB85/00392; British Patent Application Publication No. GB2188638A; Amit et al., Science, 233:747-753 (1986); Queen et al., Proc. Natl. Acad. Sci. USA, 86: 10029-10033 (1989); WO 90/07861; Riechmann et al., Nature, 332:323-327 (1988); Huse et al., Science, 246:1275-1281 (1988)).

The inoculum for polyclonal antibody production is typically prepared by dispersing the epitope or the epitope-immunocarrier conjugate in a physiologically tolerable diluent such as saline, to form an aqueous composition. An immunostimulatory amount of the inoculum preferably with adjuvant is administered to a mammal and the inoculated mammal is then maintained for a time period sufficient for the antigen to induce protective anti-*S. aureus* antibodies. After suitable periods of time, two weeks until four months, boosting doses of the antigen-immunocarrier may be applied and the antigen titer is monitored. At a suitable point, when the titer of the neutralizing or opsonic antibodies is at its peak, the antibodies are collected. Such antibodies can include antibody preparations from a variety of commonly used animals (such as mice, goats, primates, donkeys, rabbits or horses) and humans, whereby the antibodies are isolated from blood donations.

The antibodies induced in the mammal are harvested, isolated and purified to the extent desired by well-known techniques such as by alcohol fractionation and column chromatography or preferably by immunoaffinity chromatography whereby the antigen is bound to a chromatographic column. The antiserum passes the column whereby specific antibodies are retained and all other components of the serum are washed out. Then the purified antibodies are eluted with suitable gradients. A further purification may be required.

Alternatively, monoclonal antibodies can be prepared according to techniques well-known to the person skilled in the art. When a suitable monoclonal antibody is obtained, the binding regions can be identified and the whole antibody molecule as well as derivatives of the antibody like antibody fragments or subfragments can be provided. The general technique to produce monoclonal antibodies is amply described in textbooks. After having made the hybridomas or having selected the monoclonal antibody from libraries or genetically engineered animals it has to be determined to which part of the polypeptide of SEQ ID NO: 1 to 3 the moAb actually binds. Then, it has to be checked whether the antibody is protective, preferably in vivo.

Yet another aspect of the present invention then relates to a monoclonal antibody or fragment thereof which reacts specifically with at least one polypeptide epitope sequence selected from the group of SEQ ID NO: 4 to SEQ ID NO: 6, or said at least one polypeptide epitope sequence when covalently bound to an immunocarrier, preferably an antibody or fragment thereof having Complementarity-determining regions (CDRs) selected from SEQ ID NO: 15 to SEQ ID NO: 32, preferably SEQ ID NO: 15 to 20; SEQ ID NO: 21 to 26, or SEQ ID NO: 27 to 32. Preferred is the antibody or fragment thereof according to the invention which is characterized in that said antibody or fragment thereof is protective against infection caused by *Staphylococcus aureus*, in particular MRSA.

Yet another aspect of the present invention then relates to a medicament for the treatment or the prevention of a bacterial infection, characterized in that it contains at least one antibody or fragment thereof according to the present invention, wherein said bacterial infection is preferably caused by *Staphylococcus aureus*, in particular MRSA.

The antibody may be used in methods for treating or preventing an infection. Accordingly, still another subject of the invention relates to a pharmaceutical composition comprising the antibody of the invention. The pharmaceutical composition may encompass further components as detailed above for the vaccine.

Medicaments according to the present invention contain at least one antibody or active fragment thereof, but can contain 2, 3, 4 and to up to 9 antibodies according to the present invention. Preferred is a medicament comprising at least one "set" of antibodies or active fragments thereof specifically directed against each of the polypeptide epitope according to the present invention. Of course, also mixtures of antibodies or active fragments thereof specifically directed against 2, 3, and up to 9 of the antigens according to the present invention can be formulated into a medicament according to the present invention.

Yet another aspect of the present invention then relates to a diagnostic composition, comprising at least one polypeptide epitope sequence selected from the group of SEQ ID NO: 4 to SEQ ID NO: 14, and/or at least one antibody or fragment thereof, together with suitable auxiliary agents.

Yet another aspect of the present invention then relates to a nucleotide sequence encoding for a polypeptide epitope sequence selected from the group of SEQ ID NO: 4 to SEQ ID NO: 14, or an expression vector expressing said nucleotide sequence. Yet another aspect of the present invention then relates to a host cell, in particular microbial host cell, transformed with the nucleotide sequence and/or expression vector according to the invention. Yet another aspect of the present invention then relates to a method for producing a polypeptide epitope sequence selected from the group of SEQ ID NO: 4 to SEQ ID NO: 14, the method comprising culturing the host cell according to the invention, and isolating said polypeptide epitope from said cell and/or the culture medium thereof.

Yet another aspect of the present invention then relates to a method for producing a polypeptide epitope sequence selected from the group of SEQ ID NO: 4 to SEQ ID NO: 14, wherein said polypeptide epitope sequence is artificially produced, in particular as a pharmaceutically acceptable salt.

The invention also relates to a method for vaccinating a human or animal against *Staphylococcus aureus* comprising administering to said human a pharmaceutical composition according to the present invention as described. An active vaccine is administered to the patient preferably before an infection occurs. Such vaccination can therefore be applied regularly to patients at risk (e.g. elderly people, patients before solid organ or bone-marrow transplants) in order to stimulate their immune response and to avoid an infection in a hospital or a nursing home.

The polypeptides or fragments thereof either alone or coupled to an immunocarrier may further be used for the treatment or the prevention of bacterial infections. Another aspect of the present invention thus is a method for treating or preventing *Staphylococcus aureus* infection in a human or animal, comprising administering to said human or animal a medicament as described herein. Preferably, said *Staphylococcus aureus* is MRSA.

Medicaments and/or vaccines according to the present invention contain at least one polypeptide epitope, but can contain 2 to up to 9 epitopes according to the present invention. Preferred is a vaccine comprising at least one "set" of epitope fragments of at least one antigen as described, wherein said set is composed of 1, 2, 3 and up to 10 active fragments of said at least one antigen as described. The vaccine may also contain a mix of active fragments (epitopes) derived from antigens according to the present invention, i.e. SEQ ID Nos. 1 to 3.

As mentioned above, the polypeptide epitopes either alone or coupled to an immunocarrier may be used for the treatment or the prevention of Staphylococcal infections. The prevention of bacterial infection achieved by regularly application of the vaccine to patients of risk such as elderly people, infants and patients undergoing dialysis or before organ or bone-marrow transplantation so antibodies had been generated through the stimulation of the immune response.

The present invention also provides a method for producing an antibody according to the invention, characterized by the following steps: (a) administering an effective amount of the epitope according to the invention to an animal; and (b) isolating the antibody produced by the animal in response to the administration of step (a) from the animal.

Another subject of the invention relates to a method for producing an antibody according to the invention, characterized by the following steps: (a) contacting a B cell with an effective amount of the epitope according to the invention; (b) fusing the B cell of step (a) with a myeloma cell to obtain a hybridoma cell; and (c) isolating the antibody produced by the cultivated hybridoma cell. More particularly, the antibody may be produced by initiating an immune response in a non-human animal by administrating a peptide of the invention to an animal, removing an antibody containing body fluid from said animal, and producing the antibody by subjecting said antibody containing body fluid to further purification steps. Alternatively, the antibody may be produced by initiating an immune response in a non-human animal by administrating an antigen/epitope, as defined in the present invention, to said animal, removing the spleen or spleen cells from said animal and/or producing hybridoma cells of said spleen or spleen cells, selecting and cloning hybridoma cells specific for said epitope, and producing the antibody by cultivation of said cloned hybridoma cells.

The present invention will now be described further in the following examples with reference to the accompanying Figures and the Sequence Listing, nevertheless, without being limited thereto. For the purposes of the present invention, all references as cited herein are incorporated by reference in their entireties.

FIG. 1 shows the survival of mice challenged with *S. aureus* upon passive immunization with monoclonal antibodies. BALB/c mice (n=10) immunized with 300 µg monoclonal antibody or PBS as a control were infected i.p. with $5 \times 10^5$ cfu *S. aureus* mixed with 5% mucin from porcine stomach. Survival was monitored for 6 days.

FIG. 2 shows the competition of moAb binding to recombinant protein by linear epitope peptides 5 µg/mL of the respective antigen (A: hp2160, B: pOxi) was coated on a maxisorp plate. The respective peptides (hp2160-peptide, pOxi-BSA), the whole recombinant proteins (hp2160, pOxi) or an irrelevant protein were diluted and added to the plate, respectively. The respective moAb (A: anti-hp2160 moAb 16-2, B: anti-pOxi moAb D3) was added. Incubation with goat anti-mouse-HRP followed. ELISA was developed using TMB substrate and absorbance was measured at 450 nm.

FIG. 3 shows a schematic overview of Triiso fragment cloning for binding analysis of anti-Triiso moAb H8. Fragments of different Triiso sections (dark grey) were cloned and overexpressed in *E. coli* BL21. Bacteria cells were harvested and lysed for binding of moAb H8 by Western blot. The essential parts for moAb binding were marked in light gray.

FIG. 4 shows Western blot analysis of anti-Triiso moAb H8 binding to Triiso fragments. Different sections of the Triiso molecule were cloned (fused with Strep-tag) and overexpressed in *E. coli* BL21. Lysates were blotted and analyzed for antibody binding. A+B: Peptides 4, 5 and 6; C: Peptide 15. A+C: anti-Triiso moAb H8 as $1^{st}$ antibody, goat anti-mouse-HRP as $2^{nd}$ antibody; B: Strep-Tactin-HRP conjugate. IB: Preparation of inclusion bodies. CF: Cytoplasmic fraction.

FIG. 5 shows specific binding of monoclonal antibodies to the isolated cell wall-associated protein fraction of *S. aureus*. Cell wall-associated protein fraction was isolated from *S. aureus* JE2 (wt) and a protein A deletion mutant (ΔSpA) by a LiCl method and was precipitated with 10% TCA. 30 µg of this non-enzymatic cell wall supernatant (neCWS) was blotted on a nitrocellulose membrane. NeCWS was incubated with anti-hp2160 moAb 16-2 (A), anti-Triiso moAb H8 (B) and anti-pOxi moAb D3 (C), respectively. A chemiluminescent detection followed after incubation with anti-mouse-HRP conjugate.

FIG. 6 shows specific binding of anti-pOxi moAb D3 to the surface of *S. aureus*. *S. aureus* ΔSpA was grown to an $OD_{600}$ of 0.3. Harvested and washed cells were incubated with 50 µg of anti-pOxi moAb D3 (red line), 50 µg moAb D3+100 µg pOxi epitope peptide as competitor (blue line), 50 µg moAb D3+100 µg hp2160 epitope peptide (green line) or with just an equal volume of PBS (black line) in PBS+1% BSA. All samples were then incubated with 2 µg of $F(ab)_2$ anti-mouse-IgG-PE-Cy5.5. A: *S. aureus* JE2 (wildtype), B: *S. aureus* JE2-ΔSpA. Samples were measured by flow cytometry.

FIG. 7 shows the binding analysis of moAbs to the surface of *S. aureus* harvested at different growth phases. *S. aureus* ΔSpA was grown to the $ODs_{600}$ 0.1 (blue line), 0.3 (red line) and 3.0 (green line). Harvested and washed cells were first incubated with PBS (black line, A-C) 50 µg of anti-pOxi moAb D3 (A), anti-Triiso moAb H8 (B) and anti-hp2160 moAb 16-2 (C) and then with 2 µg of $F(ab)_2$ anti-mouse-IgG-PE-Cy5.5. Samples were measured by flow cytometry.

FIG. 8 shows a comparison of Triiso's occurrence in the isolated cell wall-associated protein fraction at low pH after biofilm growth of *S. aureus*. *S. aureus* was grown under biofilm conditions in TSB+0.5% Glucose for 24 h. The harvested cell pellet was resuspended in PBS of a pH of 5 and 7.5, respectively for 1 h. After centrifugation the supernatants were collected and precipitated with 10% TCA. The precipitates were washed and dissolved in 8 M Urea. 30 µl of each sample was blotted on nitrocellulose and incubated with first the respective moAb and then anti-mouse-HRP conjugate. The blot was developed by chemiluminescence for *S. aureus* ATCC29213, anti-Triiso moAb H8, and *S. aureus* ΔSpA, anti-pOxi moAb D3.

FIG. 9 shows specific binding of moAbs to the surface of *S. aureus* ΔspA after biofilm growth. *S. aureus* ΔspA was grown for 24 h under biofilm conditions. A-C: Detached and washed cells (pH 5.0) were fixed and incubated with the respective anti-*S. aureus* moAb, mouse anti-His-tag moAb (gray line, A and B) or the same volume of PBS (black line) for 30 min at 37° C. For a competition of moAb D3 binding cells were incubated with its respective epitope peptide (gray line, C). An incubation with 2 µg of F(ab)2 anti-mouse-IgG-PE-Cy5.5 followed. Samples were measured by flow cytometry.

FIG. 10 shows serial serum dilutions and quantification of antigen-specific IgG titer kinetic during active immunization with epitope peptides. BALB/c mice (n=2) were vaccinated with the respective peptide-conjugate pOxi-BSA, hp2160-BSA and TriisoC4-BSA and boosted twice. Blood was collected prior to (not shown) and post immunization and every week after the last boost. Sera were analyzed for antigen-specific IgGs by ELISA. The IgG titer is given as the dilution corresponding to the half maximal absorbance at 450 nm. Error barrs indicate mean value±SEM. A-C: serial dilutions (1:200-1:1.56×10$^7$) of serum prepared 10 days post last boost. D-F: logarithmic IgG titer kinetic during immunization.

FIG. 11 shows the immune response after immunization with hp2160-KLH. BALB/c mice (n=10) were vaccinated with hp2160 epitope peptide conjugated to KLH or with KLH as a control. Serum of every mouse was collected after the last boost and analyzed for hp2160-specific IgGs by ELISA and Western blot. A: Logarithmic antigen-specific IgG titer. The titer is given as the dilution corresponding to the half maximal absorbance at 450 nm. P-value was analyzed by Mann-Whitney test: p≤0.001=***. B: neCWS and WCL of *S. aureus* ΔSpA or wt, respectively, were blotted on a nitrocellulose membrane. Serum after the $1^{st}$ boost was pooled and incubated with the membrane, followed by detection with anti-mouse-HRP.

FIG. 12 shows the bacterial load in organs of mice after challenge with *S. aureus* upon monovalent immunization with hp2160 peptide. BALB/c mice (n=10) were immunized with hp2160 epitope peptide conjugated to KLH (green) or with KLH alone (black) as a control. After the second boost, mice were challenged i.p. with 4.5×10$^6$ CFU of *S. aureus* USA300 mixed with 5% mucin from porcine stomach. Bacterial density of liver (A), spleen (B) and kidneys (C) was determined. P-values were analyzed by Mann-Whitney test. p≤0.001=*; p=0.01=; p≤0.05=*; ns=not significant.

FIG. 13 shows the immune response after immunization with pOxi-KLH. BALB/c mice (n=10) were vaccinated with pOxi epitope peptide conjugated to KLH or with KLH as a control. Serum of every mouse was collected after the last booster immunization and analyzed for pOxi-specific IgGs by ELISA and Western blot. A: Logarithmic antigen-specific IgG titer. The titer is given as the dilution corresponding to the half maximal absorbance at 450 nm. P-value was analyzed by Mann-Whitney test: p≤0.001=***. B: Recombinant pOxi and KLH protein were blotted on a nitrocellulose membrane. Serum after the 1$^{st}$ boost was pooled and incubated with the membrane, followed by detection with anti-mouse-HRP.

FIG. 14 shows the bacterial load in organs of mice after challenge with S. aureus upon monovalent immunization with pOxi peptide. BALB/c mice (n=10) were immunized with pOxi epitope peptide conjugated to KLH (blue) or with KLH (black) as a control. After the second boost mice were challenged i.p. with 4.2×10$^6$ CFU of S. aureus USA300 mixed with 5% mucin from porcine stomach. Bacterial density of liver (A), spleen (B) and kidneys (C) was determined. P-values were analyzed by Mann-Whitney test. p≤0.001=*; p=0.01=; p≤0.05=*; ns=not significant.

FIG. 15 shows the antigen-specific IgG titer after immunization with hp2160-KLH+pOxi-KLH. BALB/c mice (n=2) were vaccinated with a combination of hp2160 and pOxi epitope peptide conjugated to KLH or with KLH as a control. Serum of every mouse was collected after the last booster immunization and analyzed for hp2160-(A) and pOxi-specific IgGs (B) by ELISA. The IgG titer is given as the dilution corresponding to the half maximal absorbance at 450 nm. P-value was analyzed by Mann-Whitney test: p≤0.001=***.

FIG. 16 shows the bacterial load in organs of mice after challenge with S. aureus upon bivalent immunization with pOxi and hp2160 peptide. BALB/c mice (n=10) were immunized with hp2160 and pOxi epitope peptides conjugated to KLH (dark gray) or with KLH (black) as a control. After the second boost mice were challenged i.p. with 4.2×10$^6$ CFU of S. aureus USA300 mixed with 5% mucin from porcine stomach. Bacterial density of liver (A), spleen (B) and kidneys (C) was determined. P-values were analyzed by Mann-Whitney test. p≤0.001=*; p=0.01=*; p≤0.05=*; ns=not significant.

FIG. 17 shows the cloning strategy of triepitope fusion-peptide. Sequences encoding the epitopes of anti-pOxi moAb D3, anti-hp2160 moAb 16-2 and Triiso fragment where epitope of anti-Triiso moAb H8 is located were cloned consecutively and N-terminal fused to Strep-tag and C-terminal fused to His-tag.

FIG. 18 shows the binding of monoclonal antibodies to triepitope peptide. 10 µg of purified triepitope peptide was blotted on a nitrocellulose membrane. Membrane was incubated with anti-pOxi moAb D3 (A), anti-hp2160 moAb 16-2 (B) and anti-Triiso moAb H8 (C). Incubation with goat anti-mouse-HRP membrane followed. Membrane was developed using chemiluminescence reagent (ECL).

FIG. 19 shows the antigen-specific IgG titer kinetic during active immunization with triepitope peptide. BALB/c mice (n=2) were vaccinated with triepitope peptide conjugated to KLH and boosted twice. Blood was collected post immunization and every week after the last boost. Sera were analyzed for antigen-specific IgGs (A: anti-hp2160, B: anti-pOxi, C: anti-Triiso) by ELISA. The IgG titer is given as the dilution corresponding to the half maximal absorbance at 450 nm. Error bars indicate mean value±SEM.

FIG. 20 shows the antigen-specific IgG titer after immunization with triepitope-KLH. BALB/c mice were vaccinated with triepitope peptide (n=11) conjugated to KLH or with KLH (n=12) as a control. Serum of every mouse was collected after the last booster immunization and analyzed for pOxi-, Triiso and hp2160-specific IgGs by ELISA. The IgG titer is given as the dilution corresponding to the half maximal absorbance at 450 nm.

FIG. 21 shows the bacterial load in organs challenged with a sublethal dose of S. aureus upon triepitope peptide immunization. BALB/c mice (n=11-12) were immunized with recombinant triepitope peptide conjugated to KLH (red) or with KLH (black) as a control group. After the second boost mice were challenged i.p. with 5.19×10$^6$ CFU of S. aureus USA300 mixed with 5% mucin from porcine stomach. Bacterial density of liver (A), spleen (B) and kidneys (C) was determined. P-values were analyzed by Mann-Whitney test. p≤0.001=*; p=0.01=; p≤0.05=*; ns=not significant.

FIG. 22 shows the cloning strategy of diepitope fusion-peptides OTO, pOT and TpO. Sequences encoding the epitopes of anti-pOxi moAb D3 and of anti-Triiso moAb H8 (Triiso fragment) were cloned consecutively into pPSG-IBA43 resulting in N-terminal fusion to Strep-tag and C-terminal fusion to His-tag. OTO: Triiso fragment surrounded by C- and N-terminal pOxi epitope; pOT: N-terminal pOxi epitope; TpO: N-terminal pOxi epitope.

FIG. 23 shows the antigen-specific IgG titer after immunization with diepitopes. BALB/c mice (n=11) were vaccinated with unconjugated diepitope peptides OTO and pOT. Serum of every mouse was collected after the last booster immunization and analyzed for pOxi-, Triiso and hp2160-specific IgGs by ELISA. The IgG titer is given as the dilution corresponding to the half maximal absorbance at 450 nm.

FIG. 24 shows the bacterial load in organs challenged with a sublethal dose of S. aureus upon immunization with diepitope peptides OTO and pOT. BALB/c mice (n=10) were immunized with recombinant diepitope peptides OTO (gray) and pOT (dark gray) or with PBS (black) as a control. After the second boost, mice were challenged i.p. with 5.4×10$^6$ CFU of S. aureus USA300 mixed with 5% mucin from porcine stomach. Bacterial density of liver (A), spleen (B) and kidneys (C) was determined. P-values were analyzed by Mann-Whitney test. p≤0.001=*; p=0.01=; p≤0.05=*; ns=not significant.

FIG. 25 shows the survival of mice challenged with an LD$_{50}$ of S. aureus upon diepitope peptide immunization. BALB/c mice (n=11) immunized with pOT-KLH (g) or KLH (black) as a control were infected i.p. with 1.2×10$^7$ cfu S. aureus USA300 mixed with 5% mucin from porcine stomach. Survival was monitored for 6 days. p-value (0.005) was determined by Gehan-Breslow test.

FIG. 26 shows the survival of mice challenged with S. aureus upon immunization with pOxi-BSA or pOT-KLH. BALB/c mice (n=11) immunized with pOxi-BSA (dark gray), pOT-KLH (gray) or a combination of BSA and KLH (black) as a control group, were infected i.p. with 3.3×10$^7$ cfu S. aureus USA300 mixed with 5% mucin from porcine stomach. Survival was monitored for 6 days. Given is exact p-value determined by Gehan-Breslow test.

FIG. 27 shows the survival of mice challenged with S. aureus upon passive immunization with protective monoclonal antibodies against S. aureus antigens. BALB/c mice (n=8-10) immunized with 200 µg monoclonal antibody (colored) or PBS (black) as a control were infected i.p. with lethal cfu of S. aureus mixed with 5% mucin from porcine stomach and survival was monitored for 6 days.

FIG. 28 shows that the protective effect of antibodies against S. aureus antigens is epitope-specific. Protective (16-2) and non-protective (35-6) anti-S. aureus hp2160 monoclonal antibodies (moAb): BALB/c mice (n=10)

immunized with 200 μg monoclonal antibody (colored) or PBS (black) as a control were infected i.p. with lethal cfu of S. aureus mixed with 5% mucin from porcine stomach and survival was monitored for 6 days.

FIG. 29 shows the AS-sequence of S. aureus hp2160 (SEQ ID NO. 3). The linear epitope of moAb 16-2 (underline) was identified by microarray technology using overlapping 13mer hp2160 peptides. Epitope of moAb 35-6 is unknown but distinct from moAb 16-2 epitope at the C-terminus of hp2160, analyzed by Western blotting with hp2160 fragments (data not shown).

FIG. 30 shows that the non-protective moAb 35-6 does not compete with protective moAb 16-2 for binding to hp2160. Binding of DyLight-649 conjugated anti-hp2160 moAb 16-2 to recombinant hp2160 coated on ELISA Max-iSorp plate, was competed with unconjugated, indicated moAbs. Binding was determined by fluorescence measurement (Ex 493/Em 518) and compared to control sample (no competitor, 100% binding).

FIG. 31 shows protective (H8, F3) and non-protective (C4) anti-S. aureus Triiso antibodies; BALB/c mice (n=10) immunized with 200 μg monoclonal antibody (colored) or PBS (black) as a control were infected i.p. with lethal cfu of S. aureus mixed with 5% mucin from porcine stomach and survival was monitored for 6 days. See also FIG. 27.

FIG. 32 shows the 3D-backbone of S. aureus Triiso with known anti-Triiso moAb C4 epitope (identified by microarray technology using overlapping 13mer Triiso peptides). Anti-Triiso moAb C4 is non-protective, whereas moAbs H8 and F3 recognising the same, discontinuous epitope, are protective in S. aureus infection model.

FIG. 33 shows that non-protective moAb C4 does not compete with protective moAbs H8 & F3 for binding to Triiso. Binding of DyLight-649 conjugated anti-Triiso moAb H8 to recombinant Triiso coated on Maxisorp ELISA plate was competed with unconjugated, indicated moAbs. Binding was determined by fluorescence measurement (Ex 493/Em 518) and compared to control sample (no competitor, 100% binding).

FIG. 34 shows protective (D3) and non-protective (C8) anti-S. aureus pOxi antibodies: BALB/c mice (n=10) immunized with 200 μg monoclonal antibody (colored) or PBS (black) as a control were infected i.p. with lethal cfu of S. aureus mixed with 5% mucin from porcine stomach and survival was monitored for 6 days. See also FIG. 27.

Figure 37:
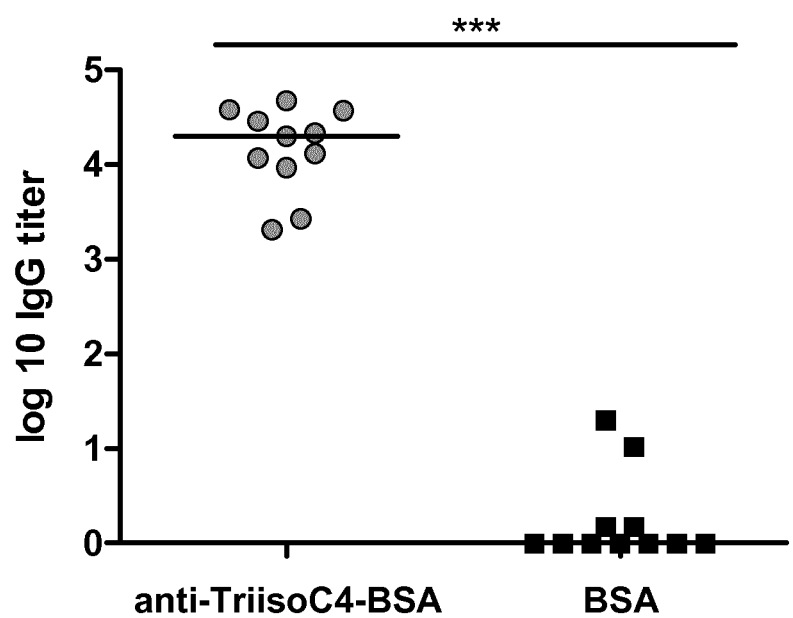
Figure 38:
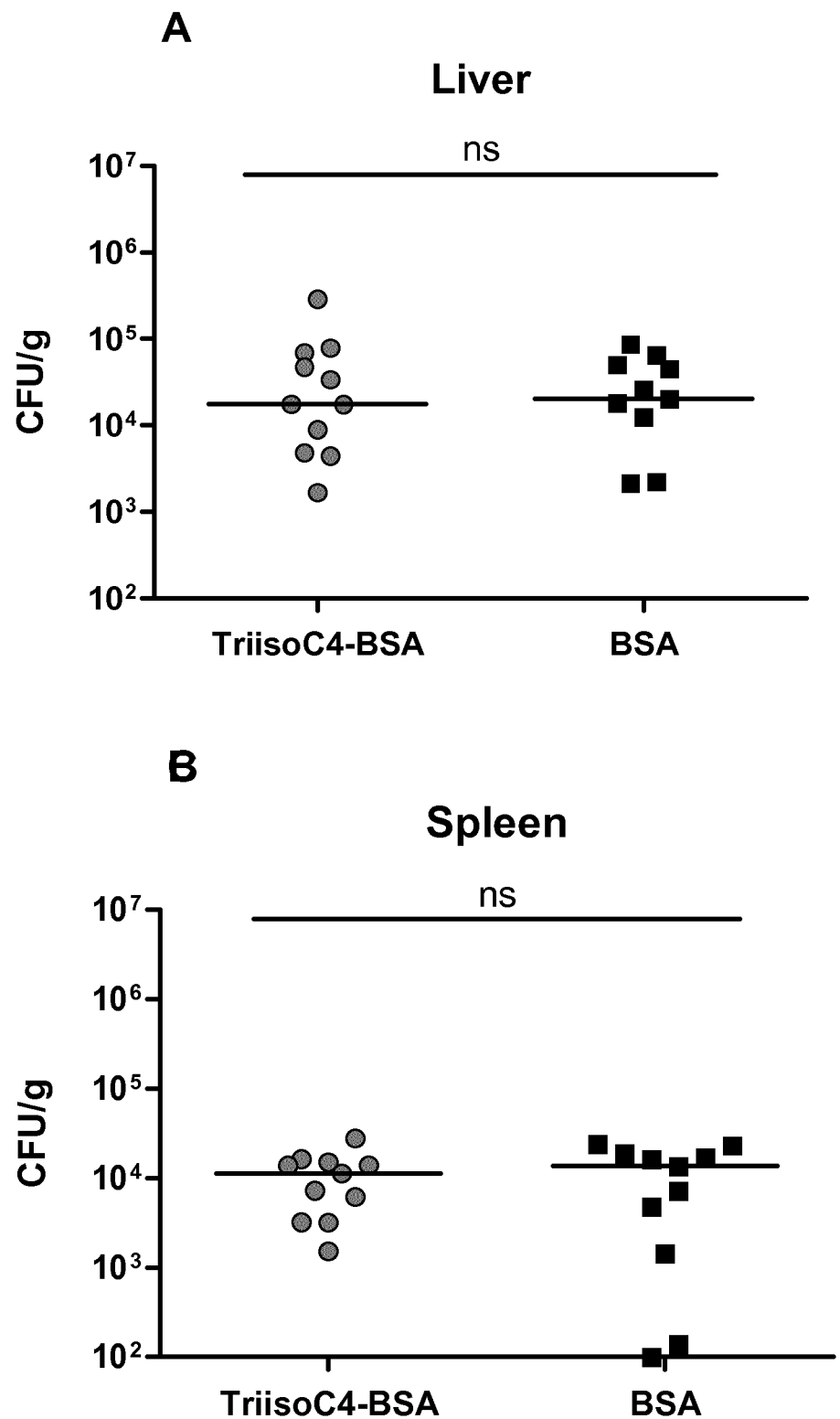

FIG. 37 shows a vaccination with non-protective TriisoC4 epitope peptide. Immune response after immunization with TriisoC4-BSA. BALB/c mice (n=11) were vaccinated with TriisoC4 epitope peptide conjugated to BSA or with BSA as a control. Serum of every mouse was collected after the last booster immunization and analyzed for Triiso-specific IgGs by ELISA (Logarithmic antigen-specific IgG titer). The titer is given as the dilution corresponding to the half maximal absorbance at 450 nm. P-value was analyzed by Mann-Whitney test: $p \leq 0.001 = ***$ FIG. 38 shows that active vaccination with cognate epitope of non-protective anti-pOxi moAb C4 does not result in protection against S. aureus infection. Bacterial load in organs challenged with a sublethal dose of S. aureus upon TriisoC4 peptide immunization. BALB/c mice (n=11) were immunized with TriisoC4 epitope peptide conjugated to BSA (orange) or with BSA (black) as a control. After the second boost mice were challenged i.p. with $4.75 \times 10^6$ CFU of S. aureus USA300 mixed with 5% mucin from porcine stomach. Bacterial density of liver (A) and spleen (B) was determined. P-values were analyzed by Mann-Whitney test. ns=not significant.

```
SEQ ID NO: 1 shows the amino acid sequence of pOxi (GenBank gi 14247604)
MTKSVAIIGAGITGLSSAYFLKQQDPNIDVTIFEASNRPGGKIQSYRKDGYMIELGPES

YLGRKTIMTELAKDIGLEQDIVTNTTGQSYIFAKNKLYPIPGGSIMGIPTDIKPFVTTKL

ISPLGKLRAGLDLIKKPIQMQDGDISVGAFFRARLGNEVLENLIEPLMGGIYGTDIDKL

SLMSTFPNFKEKEEAFGSLIKGMKDEKNKRLKQRQLYPGAPKGQFKQFKHGLSSFIEA

LEQDVKNKGVTIRYNTSVDDIITSQKQYKIVYSNQQEDVFDGVLVTTPHQVFLNWFG

QDPAFDYFKTMDSTTVATVVLAFDEKDIENTYDGTGFVIARTSDTDITACTWTSKKW

PFTTPEGKVLIRAYVGKPGDTVVDDHTDNELVSIVRRDLSQMMTFKGDPEFTIVNRLP

KSMPQYHVGHIQQIRQIQAHIKQTYPRLRVTGASFEAVGLPDCITQGKVAAEEVIAEL

SEQ ID NO: 2 shows the amino acid sequence of Triiso (GenBank WP_001260089)
MRTPIIAGNWKMNKTVQEAKDFVNALPTLPDSKEVESVICAPAIQLDALTTAVKEGK

AQGLEIGAQNTYFEDNGAFTGETSPVALADLGVKYVVIGHSERRELFHETDEEINKK

AHAIFKHGMTPIICVGETDEERESGKANDVVGEQVKKAVAGLSEDQLKSVVIAYEPI

WAIGTGKSSTSEDANEMCAFVRQTIADLSSKEVSEATRIQYGGSVKPNNIKEYMAQT

DIDGALVGGASLKVEDFVQLLEGAK
```

-continued

SEQ ID NO: 3 shows the amino acid sequence of hp2160 (GenBank WP_000620864)
MIRNRVMNSVVNKYLLHNRSIMFKNDQDVERFFYKREIENRKKHKQPSTLNVKANL

EKLSLDDMQVFRFNFRHQIDKKILYIHGGFNALQPSPFHWRLLDKITLSTLYEVVLPIY

PKTPEFHIDDTFQAIQRVYDQLVSEVGHQNVVVMGDGSGGALALSFVQSLLDNQQPL

PNKLYLISPILDATLSNKDISDALIEQDAVLSQFGVNEIMKKWANGLPLTDKRISPING

TIEGLPPVYMFGGGREMTHPDMKLFEQMMLQHHQYIEFYDYPKMVHDFPIYPIRQSH

KAIKQIAKSIDEDVTQNN

SEQ ID NO: 4 shows the epitope sequence for hp2160: KNDQDVERFFYK

SEQ ID NO: 5 shows the epitope sequence for pOxi: HTDNELVSIVRRDLSQ

SEQ ID NO: 6 shows the epitope sequence for Triiso
NKKAHAIFKHGMTPIICVGETDEERESGKANDVVGEQVKKAVAGLSEDQLKSVVIAY

EPIWAIGTGKSSTSEDANEMCAFVRQTIADLSSKEVSEATRIQYGGSVKPN

SEQ ID NO: 7 shows the epitope sequence for Triiso, loop 1; AA 1-15
(NKKAHAIFKHGMTPI), SEQ ID NO: 8 shows the epitope sequence for Triiso, loop 2; AA 49-59 (QLKSVVIAYEP), SEQ ID NO: 9 shows the epitope sequence for Triiso, loop 3; AA 74-88
(ANEMCAFVRQTIADL), SEQ ID NO: 10 shows the epitope sequence for Triiso, loop 4; AA 89-108
(SSKEVSEATRIQYGGSVKPN).

SEQ ID NO: 11 shows the triepitope peptide sequence
TDNELVSIVRRDKAHAIFKHGMTPIICVGETDEERESGKANDVVGEQVKKAVAGLSE

DQLKSVVIAYEPIWAIGTGKSSTSEDANEMCAFVRQTIADLSSKEVSEATRIQYGGSV

KPNKNDQDVERFFYK

SEQ ID NO: 12 shows the diepitope peptide sequence pOT
TDNELVSIVRRDKAHAIFKHGMTPIICVGETDEERESGKANDVVGEQVKKAVAGLSE

DQLKSVVIAYEPIWAIGTGKSSTSEDANEMCAFVRQTIADLSSKEVSEATRIQYGGSV

KPN

SEQ ID NO: 13 shows the diepitope peptide sequence OTO
TDNELVSIVRRDKAHAIFKHGMTPIICVGETDEERESGKANDVVGEQVKKAVAGLSE

DQLKSVVIAYEPIWAIGTGKSSTSEDANEMCAFVRQTIADLSSKEVSEATRIQYGGSV

KPNTDNELVSIVRRD

SEQ ID NO: 14 shows the diepitope peptide sequence TpO
KAHAIFKHGMTPIICVGETDEERESGKANDVVGEQVKKAVAGLSEDQLKSVVIAYEPI

WAIGTGKSSTSEDANEMCAFVRQTIADLSSKEVSEATRIQYGGSVKPNTDNELVSIVR

RD

SEQ ID NOs: 15 to 20 show the CDRs of moAb 16-2 (hp2160):
VH-CDR1: GYTFTDYSMH; SEQ ID NO: 15

VH-CDR2: WIDTETGEPTFADDFKG; SEQ ID NO: 16

VH-CDR3: PLLRLSFAMDS; SEQ ID NO: 17

VL-CDR1: SASENLDIYGNSFMH; SEQ ID NO: 18

VL-CDR2: RASKLES; SEQ ID NO: 19

VL-CDR3: QQTSEDPRT; SEQ ID NO: 20

SEQ ID NOs: 21 to 26 show the CDRs of moAb D3 (pOxi):
VH-CDR1: SRYWIE; SEQ ID NO: 21

VH-CDR2: EILPGSGSTNYNEKFKG; SEQ ID NO: 22

VH-CDR3: FYSGNFVGPVDY; SEQ ID NO: 23

-continued

VL-CDR1: KSSQSLSDSDGKTYLN; SEQ ID NO: 24

VL-CDR2: LVSKVDS; SEQ ID NO: 25

VL-CDR3: WQGTHFPFT; SEQ ID NO: 26

SEQ ID NOs: 27 to 32 show the CDRs of moAb H8 (Triiso)
VH-CDR1: GFTFSAYWMN; SEQ ID NO: 27

VH-CDR2: EIRMKSNNYATHYAESVKG; SEQ ID NO: 28

VH-CDR3: YKYDGAY; SEQ ID NO: 29

VL-CDR1: SASSTVNYMH; SEQ ID NO: 30

VL-CDR2: DTSKLAS; SEQ ID NO: 31

VL-CDR3: HQRSSYPT; SEQ ID NO: 32

EXAMPLES

Anchorless cell wall proteins from *S. aureus* ATCC 29213 were identified as vaccine candidates by subtractive proteome and MALDI-TOF analysis (Glowalla et al., 2009). Some of them, for example protoporphyrinogen oxidase (pOxi), triosephosphate isomerase (Triiso) and the hypothetical protein 2160 (hp2160), when used as full-length vaccines, achieved a repetitive protection in an established murine sepsis model.

In the context of the present invention, monoclonal antibodies (moAbs) were generated and three of these purified moAbs, D3 (pOxi), H8 (Triiso) and 16-2 (hp2160) were then tested for passive immunization, and demonstrated a repetitive protection in the murine sepsis model. The epitopes of these moAbs were identified and tested for their activity as a vaccine and demonstrated a repetitive protection in the murine sepsis model as well.

FIG. 1 shows the survival of mice challenged with *S. aureus* upon passive immunization with monoclonal antibodies. BALB/c mice (n=10) immunized with 300 µg monoclonal antibody or PBS as a control were infected i.p. with $5 \times 10^5$ cfu *S. aureus* mixed with 5% mucin from porcine stomach. Survival was monitored for 6 days.

A particular focus was set on pOxi, because of the prospective use of a humanized version of anti-pOxi moAb D3 in clinical studies to treat MRSA-based bacteremia, followed by the anti-Triiso antibody. Furthermore, an identification of the epitopes of the protective moAbs was performed for their application as an active vaccine.

Identification and Verification of Linear Epitopes

For this, a microarray was used to identify the epitopes of anti-hp2160 moAb 16-2 and anti-pOxi-moAb D3. Respective antigen was synthesized in fragments of 13 amino acids on a chip with overlapping of 12 amino acids. This array was incubated with moAb and goat anti-mouse IgG-DyLight680 conjugate. Read-out followed with an Odyssey Imaging System. A response of anti-hp2160 moAb 16-2, as well as anti-pOxi moAb D3 with the linear peptides (hp2160, SEQ ID NO: 4) and (pOxi, SEQ ID NO: 5) was identified, respectively.

FIG. 2 shows the competition of moAb binding to recombinant protein by linear epitope peptides. For this, 5 µg/mL of the respective antigen (A: hp2160, B: pOxi) was coated on a maxisorp plate. The respective epitope peptides (hp2160-peptide, pOxi-BSA), the whole recombinant proteins (hp2160, pOxi) or an irrelevant protein were diluted and added to the plate, respectively. The respective moAb (A: anti-hp2160 moAb 16-2, B: anti-pOxi moAb D3) was added. Incubation with goat anti-mouse-HRP followed. Then, ELISA was developed using TMB substrate and absorbance was measured at 450 nm.

Analysis of Discontinuous Epitope of Anti-Triiso moAb H8

Figure 3:
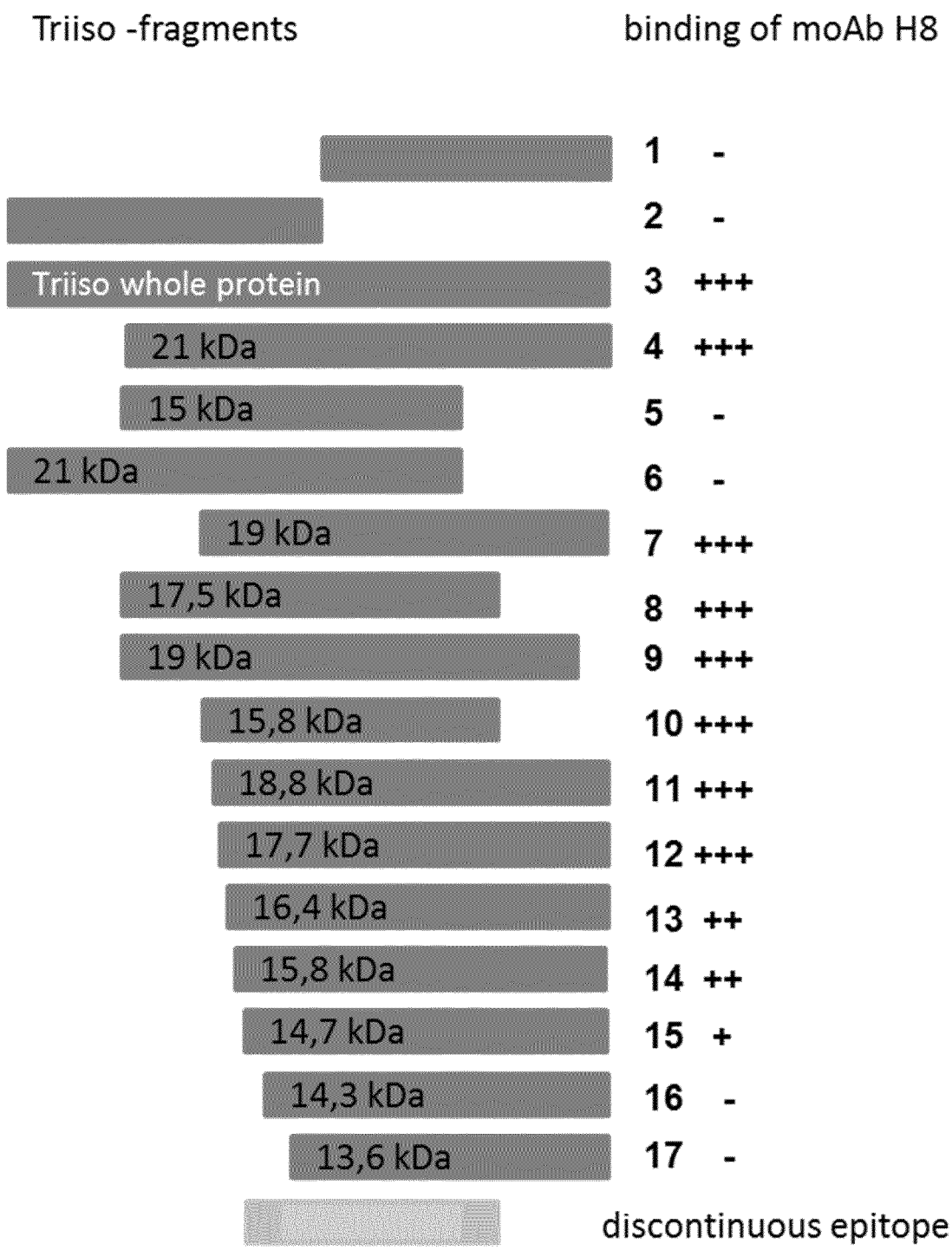

FIG. 3 shows a schematic overview of Triiso fragment cloning for a binding analysis of anti-Triiso moAb H8. Fragments of different Triiso sections (dark gray) were cloned and overexpressed in *E. coli* BL21. Bacterial cells were then harvested and lysed for subsequent binding of moAb H8 by Western blot. The essential parts for moAb binding are marked in light gray. These results were supported by full discontinuous epitope mapping using the CLIPS technology (Pepscan Presto BV., The Netherlands) leading to a stretch of 108 aa of Triiso (SEQ ID NO: 2) as the Triiso epitope (SEQ ID NO: 6) of which aa 1-15 (NKKAHAIFKHGMTPI, SEQ ID NO: 7), 49-59 (QLKSV-VIAYEP, SEQ ID NO: 8), 74-88 (ANEMCAFVRQTIADL, SEQ ID NO: 9) and 89-108 (SSKEVSEAT-RIQYGGSVKPN, SEQ ID NO: 10) resemble loops interacting with the paratope of anti-Triiso moAb H8

Figure 4:
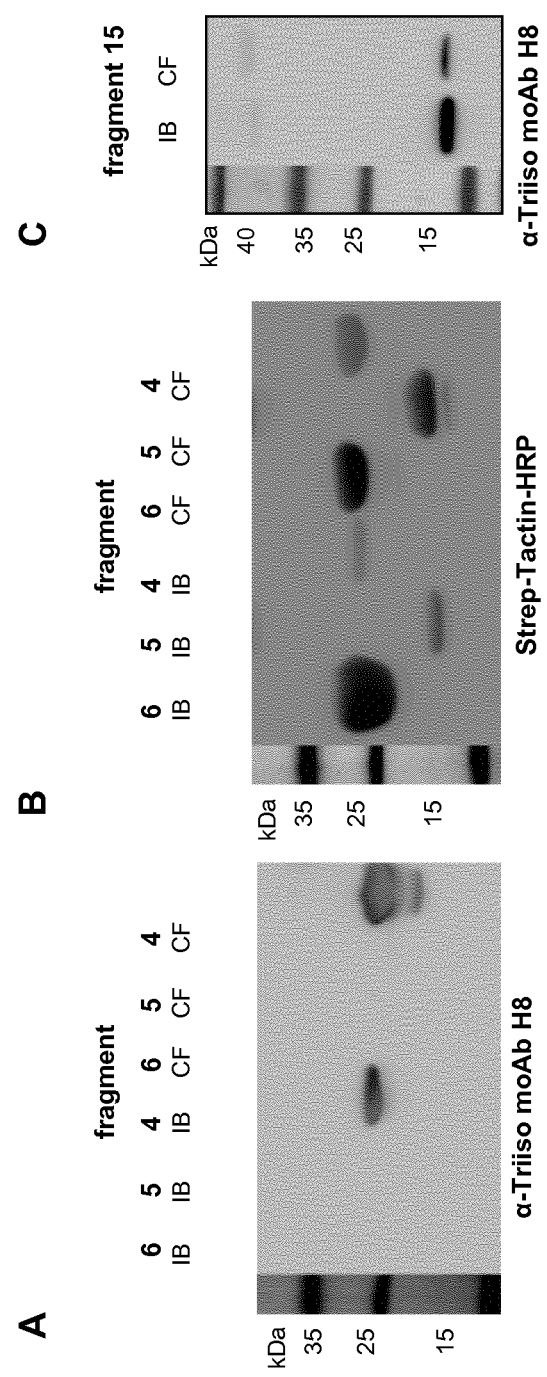

Similarly, FIG. 4 shows Western blot analysis of anti-Triiso moAb H8 binding to Triiso fragments. For this, different sections of the Triiso protein were cloned (fused with Strep-tag) and overexpressed in *E. coli* BL21. Lysates were blotted and analyzed for antibody binding. A+B: Peptides 4, 5 and 6; C: Peptide 15. A+C: anti-Triiso moAb H8 as 1$^{st}$ antibody, goat anti-mouse-HRP as 2$^{nd}$ antibody; B: Strep-Tactin-HRP conjugate. IB: Preparation of inclusion bodies. CF: Cytoplasmic fraction.

Binding Analysis of moAbs

Figure 5:
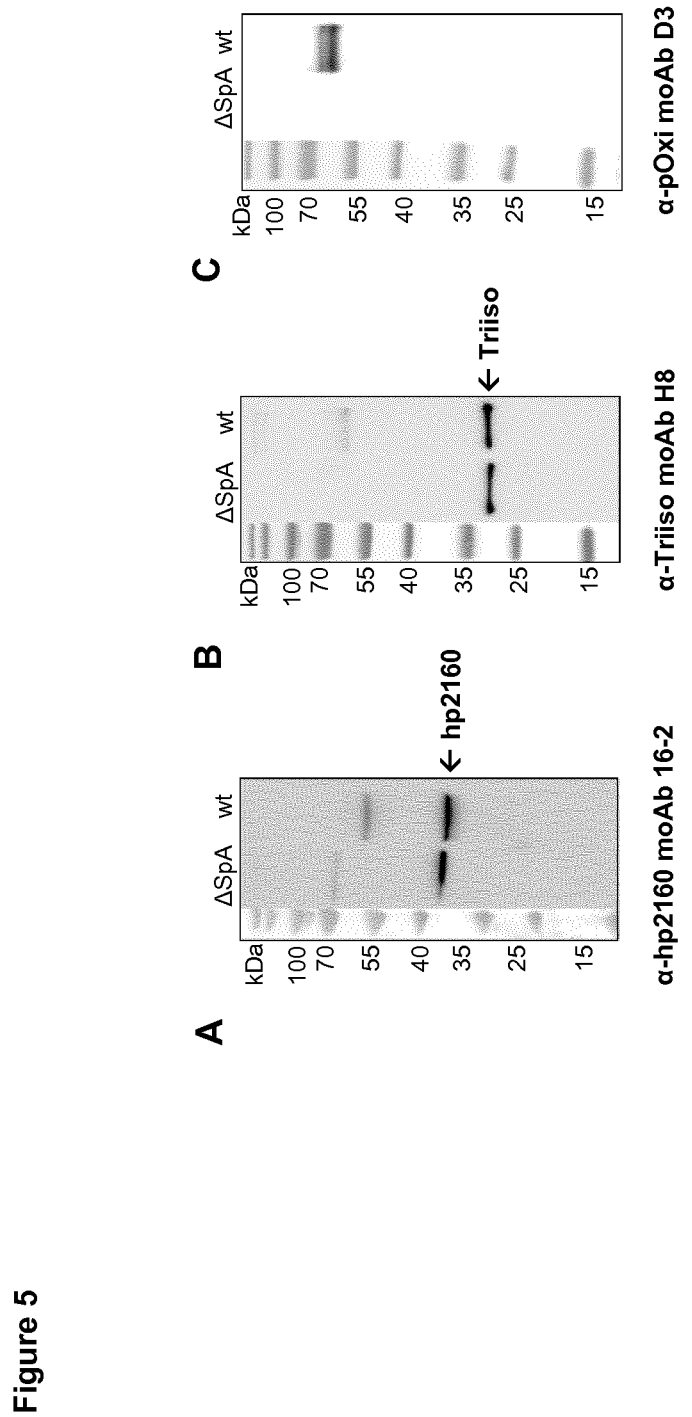

FIG. 5 shows specific binding of monoclonal antibodies to the isolated cell wall-associated protein fraction of *S. aureus*. Cell wall-associated protein fraction was isolated from *S. aureus* JE2 (wt), and a protein A deletion mutant (ΔSpA) by a LiCl method, and was precipitated with 10% TCA. 30 µg of this non-enzymatic cell wall supernatant (neCWS) was blotted onto a nitrocellulose membrane. NeCWS was then incubated with anti-hp2160 moAb 16-2 (A), anti-Triiso moAb H8 (B) and anti-pOxi moAb D3 (C), respectively. A chemiluminescent detection followed after incubation with anti-mouse-HRP conjugate.

Figure 6:
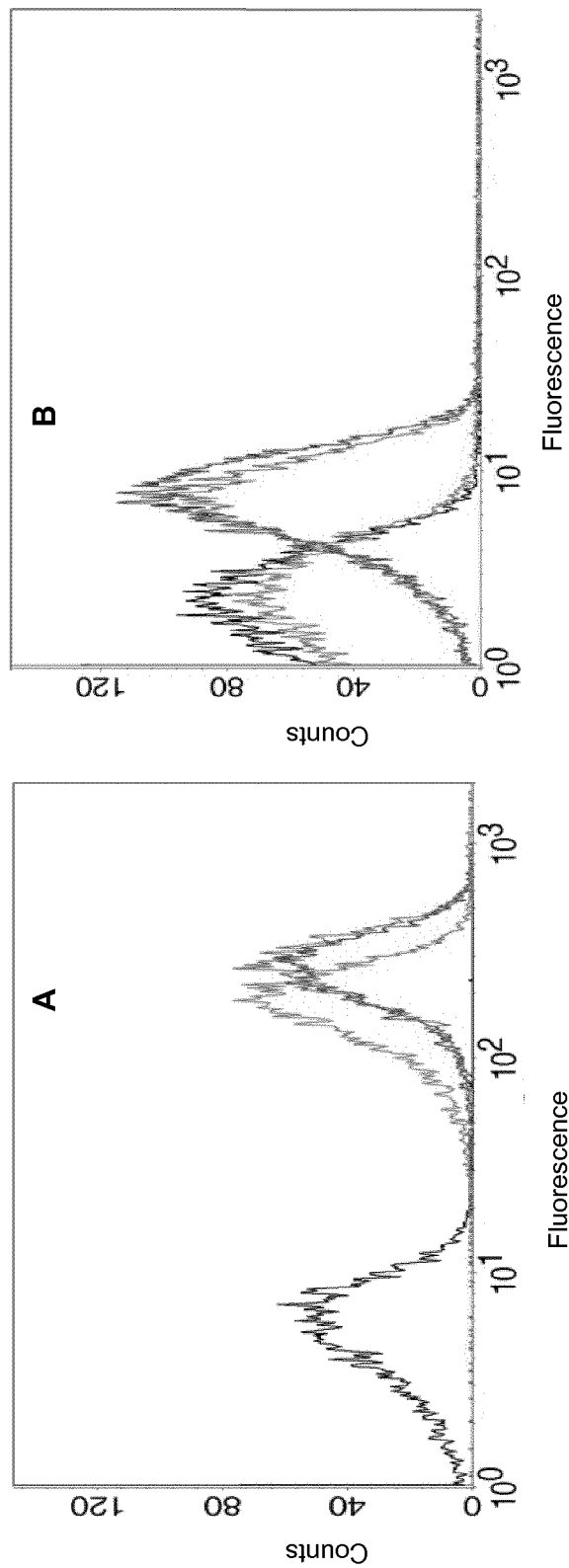

Specific Binding of Anti-pOxi moAb D3 to the *S. Aureus* Surface Under Planktonic Growth Conditions Specific binding of anti-pOxi moAb D3 to the surface of *S. aureus* was analyzed (FIG. 6). For this, *S. aureus* ΔSpA was grown to an $OD_{600}$ of 0.3. Harvested and washed cells were incubated with 50 µg of anti-pOxi moAb D3 (light gray line), 50 µg moAb D3+100 µg pOxi epitope peptide as competitor (blue line), 50 µg moAb D3+100 µg hp2160 epitope peptide (dark gray line) or with just an equal volume of PBS (black line) in PBS+1% BSA. All samples were then incubated with 2 µg of F(ab)$_2$ anti-mouse-IgG-PE-Cy5.5. A: *S. aureus* JE2 (wildtype), B: *S. aureus* JE2-ΔSpA. Samples were measured by flow cytometry.

Figure 7:
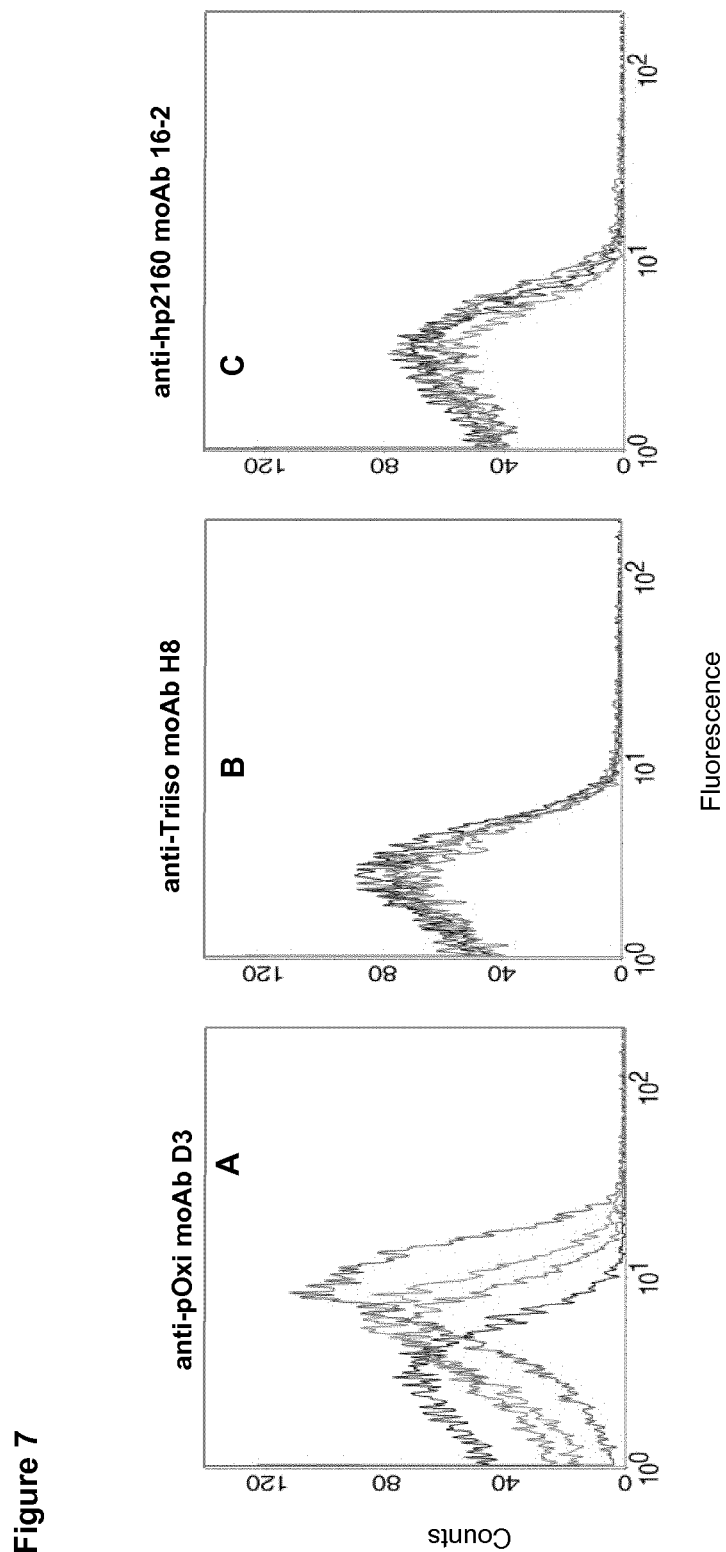

Also, the binding analysis of moAbs to the surface of *S. aureus* harvested at different growth phases was analyzed (FIG. 7). *S. aureus* ΔSpA was grown to the OD$_{600}$ 0.1 (blue line), 0.3 (red line) and 3.0 (green line). Harvested and washed cells were first incubated with PBS (black line, A-C), 50 µg of anti-pOxi moAb D3 (A), anti-Triiso moAb H8 (B) and anti-hp2160 moAb 16-2 (C) and then with 2 µg of F(ab)$_2$ anti-mouse-IgG-PE-Cy5.5. Samples were measured by flow cytometry.

Biofilm Conditions and Low pH Increase Triiso and hp2160 Presentation on *S. Aureus* Surface It was not possible to detect a binding of anti-Triiso moAb H8 and anti-hp2160 moAb 16-2 to the surface of whole *S. aureus* cells after planktonic growth. Therefore, biofilm growth conditions were simulated by growing *S. aureus* JE2 in TSB+0.5% Glucose for 24 h in 96 well plates without shaking.

Figure 8:
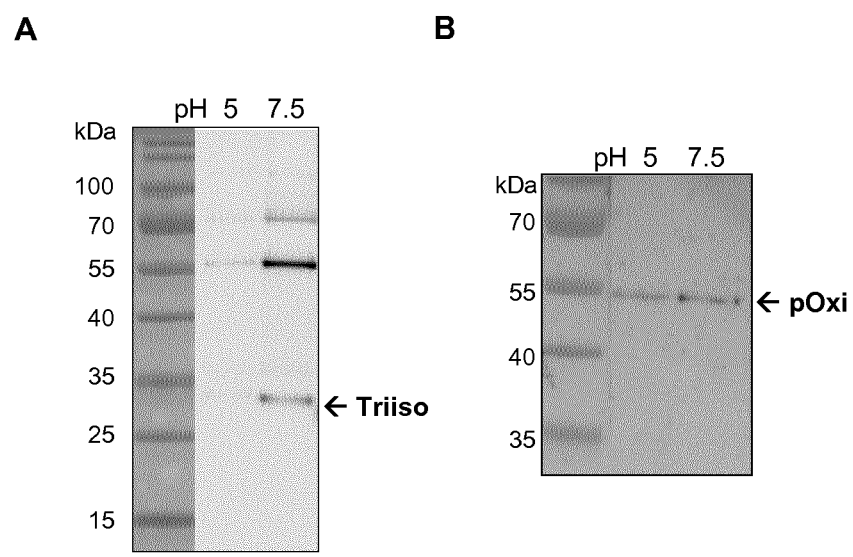

It was found that the retention of Triiso on the cell surface is pH-dependent (FIG. 8). For a comparison of Triiso's occurrence in the isolated cell wall-associated protein fraction at low and neutral pH after biofilm growth of *S. aureus*, *S. aureus* was grown under bio film conditions in TSB+0.5% Glucose for 24 h. The harvested cell pellet was resuspended in PBS of a pH of 5 and 7.5, respectively for 1 h. After centrifugation the supernatants were collected and precipitated with 10% TCA. The precipitates were washed and dissolved in 8 M Urea. 30 µl of each sample was blotted on nitrocellulose and incubated with first the respective moAb and then anti-mouse-HRP conjugate. The blot was developed by chemiluminescence for *S. aureus* ATCC29213, anti-Triiso moAb H8, and *S. aureus* ΔSpA, anti-pOxi moAb D3.

Figure 9:
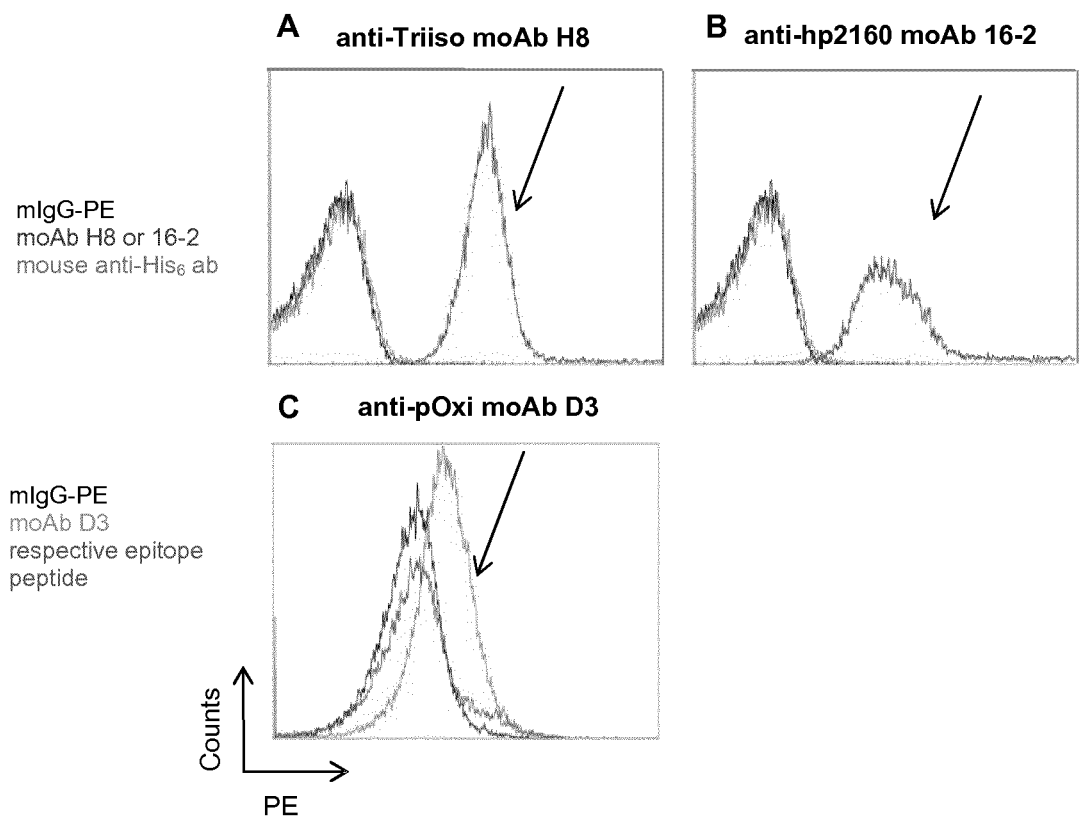

For further binding analyses of moAbs H8 and 16-2 by flow cytometry, strain ΔspA was grown for 40 h under biofilm conditions. Additionally, binding of anti-pOxi moAb D3 was also analyzed after biofilm growth, although this moAb already showed a surface binding after planktonic growth (compare FIG. 7). The detached biofilm cells were harvested and washed at a pH of 5.0 for a few times. The cell pellet was then fixed with 3% paraformaldehyde and then incubated with the respective moAb and the PE-conjugated secondary antibody (FIG. 9). For a specific binding of anti-Triiso moAb H8 and anti-hp2160 moAb 16-2 to the surface of *S. aureus* ΔSpA biofilm growth conditions were necessary.

Active Immunization with Epitope Peptides

It was shown that immunization with epitope peptides induces an antigen-specific immune response. The aim of these experiments is to study an active immunization with the epitopes of the monoclonal antibodies (moAbs) that showed protection in a murine sepsis model after passive immunization. Vaccination with the synthesized epitope peptides according to the invention should induce the production of the same protective IgGs by the organism's immune system itself.

For this, synthesized pOxi-, hp2160- and TriisoC4-peptides were either conjugated to the carrier protein bovine serum albumin (BSA) or the protein keyhole limpet hemocyanin (KLH) isolated from *Megathura crenulata*, because this improved the generation of an immune response.

Figure 10:
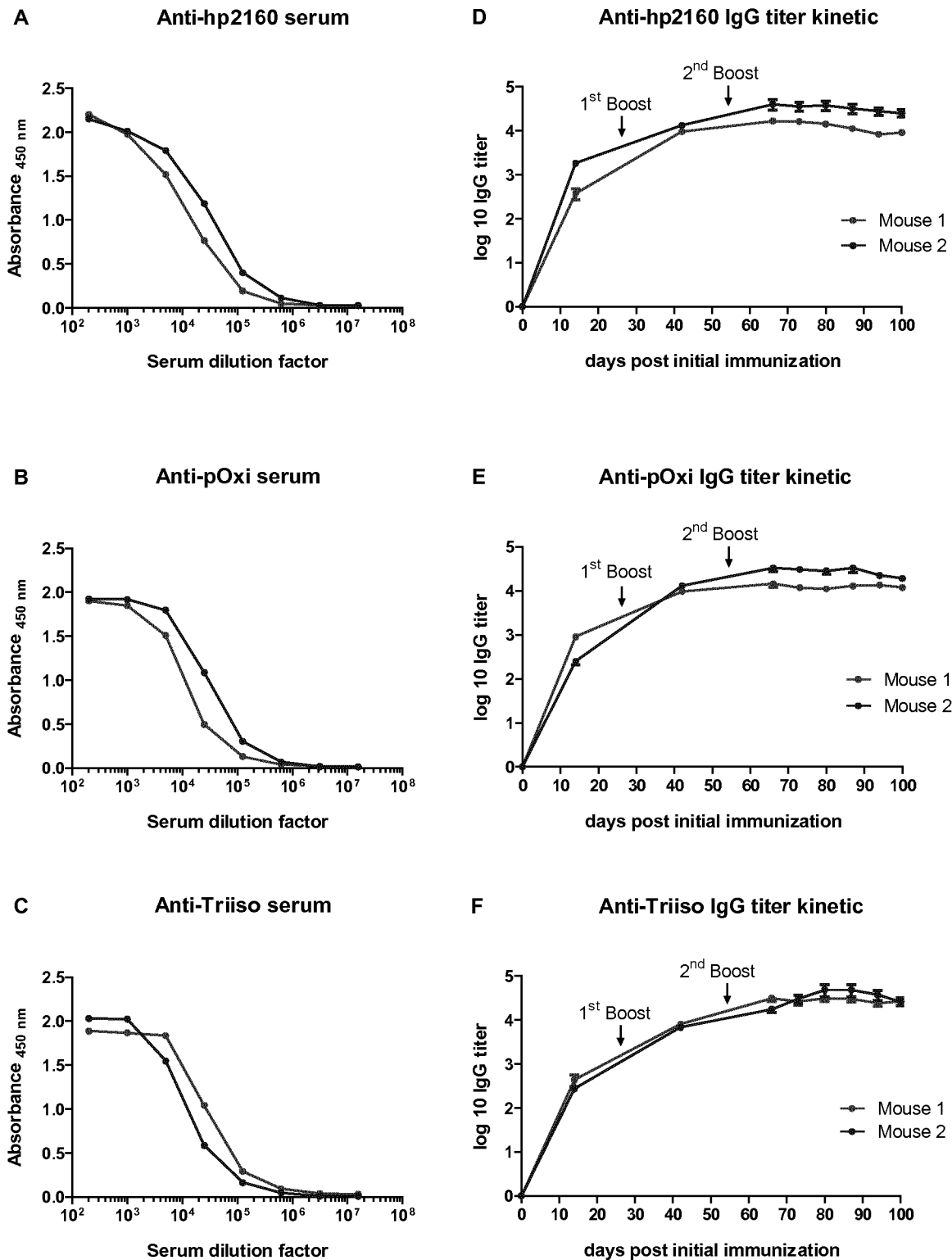

Then, BALB/c mice (n=2) were vaccinated s.c. with the respective peptide-conjugate pOxi-BSA, hp2160-BSA and Triiso C4-BSA and boosted twice (FIG. 10). Blood was collected prior to (not shown) and post immunization and every week until 50 days post the last boost. Sera were analyzed for antigen-specific IgGs by ELISA. The IgG titer is given as the dilution corresponding to the half maximal absorbance at 450 nm. Serial dilutions (1:200-1:1.56×10$^7$) of serum were prepared 10 days post last boost. Logarithmic IgG titer kinetic during immunization was determined.

It could be shown that mono- and bivalent immunization with epitope peptides leads to significant higher bacterial clearance in organs after *S. aureus* infection. For this, BALB/c mice (n=10-12) received s.c. an initial and two booster immunizations every four weeks. Blood samples were collected two weeks post immunization. After the last boost mice were challenged i.p. with a sublethal dose of *S. aureus* USA300. After 24 h mice were sacrificed and organs were prepared for a determination of the bacterial density. In case of a survival experiment mice were infected with a lethal dose and they were monitored for 6 days.

Vaccination with Anti-hp2160 moAb 16-2 Epitope Peptide (hp2160-KLH)

Figure 11:
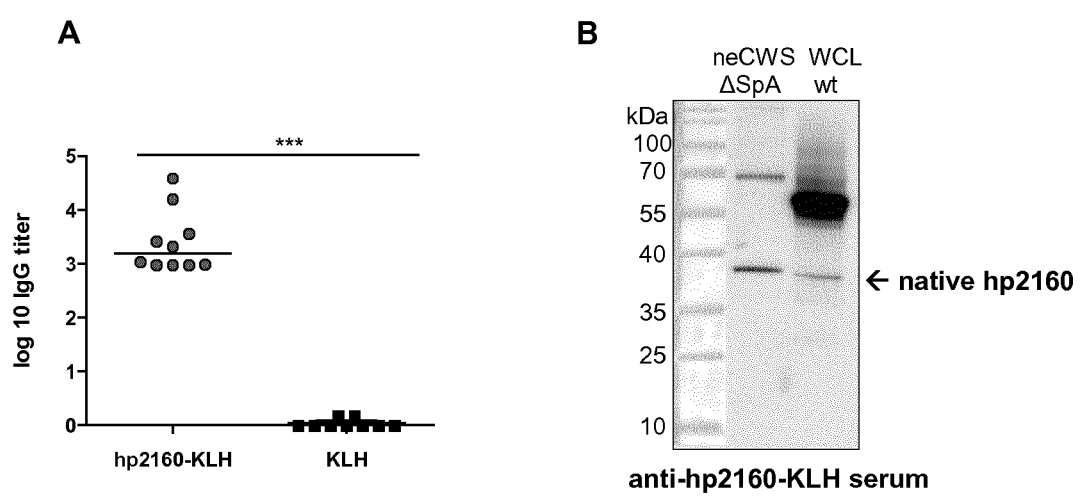

FIG. 11 shows the results for the analysis of the immune response after immunization with hp2160-KLH. BALB/c mice (n=10) were vaccinated with hp2160 epitope peptide conjugated to KLH or with KLH as a control. Serum of every mouse was collected after the last boost and analyzed for hp2160-specific IgGs by ELISA and Western blot. A: Logarithmic antigen-specific IgG titer. The titer is given as the dilution corresponding to the half maximal absorbance at 450 nm. P-value was analyzed by Mann-Whitney test: p≤0.001=***. B: neCWS and WCL of *S. aureus* ΔSpA or wt, respectively, were blotted on a nitrocellulose membrane. Serum after the 1$^{st}$ boost was pooled and incubated with the membrane, followed by detection with anti-mouse-HRP.

Figure 12:
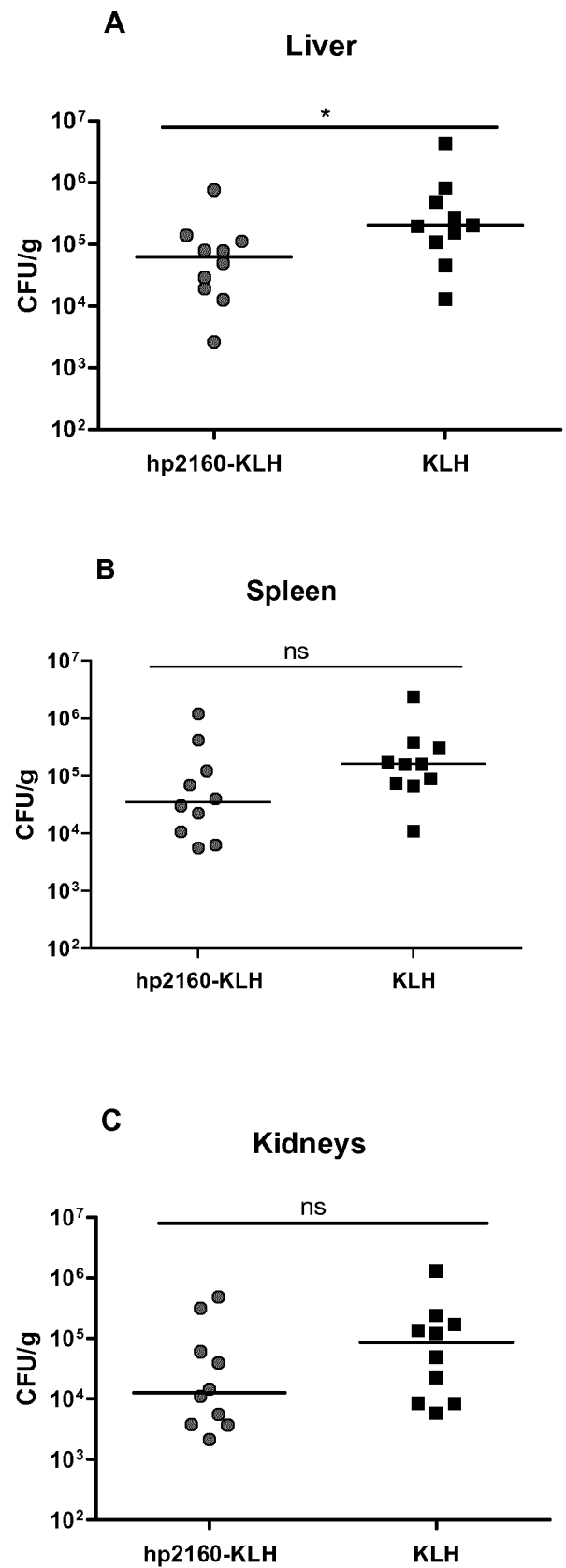

For an analysis of the bacterial load in organs of mice after challenge with *S. aureus* upon monovalent immunization with hp2160 peptide (FIG. 12), BALB/c mice (n=10) were immunized with hp2160 epitope peptide conjugated to KLH (green) or with KLH alone (black) as a control. After the second boost, mice were challenged i.p. with 4.5×10$^6$ CFU of *S. aureus* USA300 mixed with 5% mucin from porcine stomach. Bacterial density of liver (A), spleen (B) and kidneys (C) was determined. P-values were analyzed by Mann-Whitney test. p≤0.001=*; p=0.01=; p≤0.05=*; ns=not significant.

Figure 13:
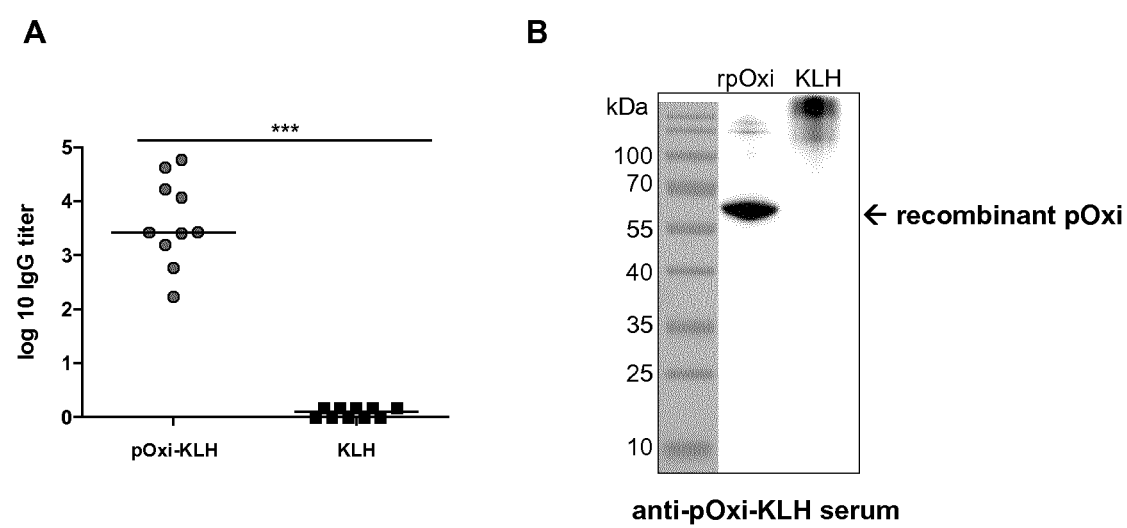

Vaccination with Anti-pOxi moAb D3 Epitope Peptide Leads to High Titer Anti-pOxi Antibodies and Provides Protective Effect in *S. Aureus* Infection Model FIG. 13 shows the results of the immune response after immunization with pOxi-KLH. BALB/c mice (n=10) were vaccinated with pOxi epitope peptide conjugated to KLH or with KLH as a control. Serum of every mouse was collected after the last booster immunization and analyzed for pOxi-specific IgGs by ELISA and Western blot. A: Logarithmic antigen-specific IgG titer. The titer is given as the dilution corresponding to the half maximal absorbance at 450 nm. P-value was analyzed by Mann-Whitney test: p≤0.001=***. B: Recombinant pOxi and KLH protein were blotted on a nitrocellulose membrane. Serum after the 1$^{st}$ boost was pooled and incubated with the membrane, followed by detection with anti-mouse-HRP.

Figure 14:
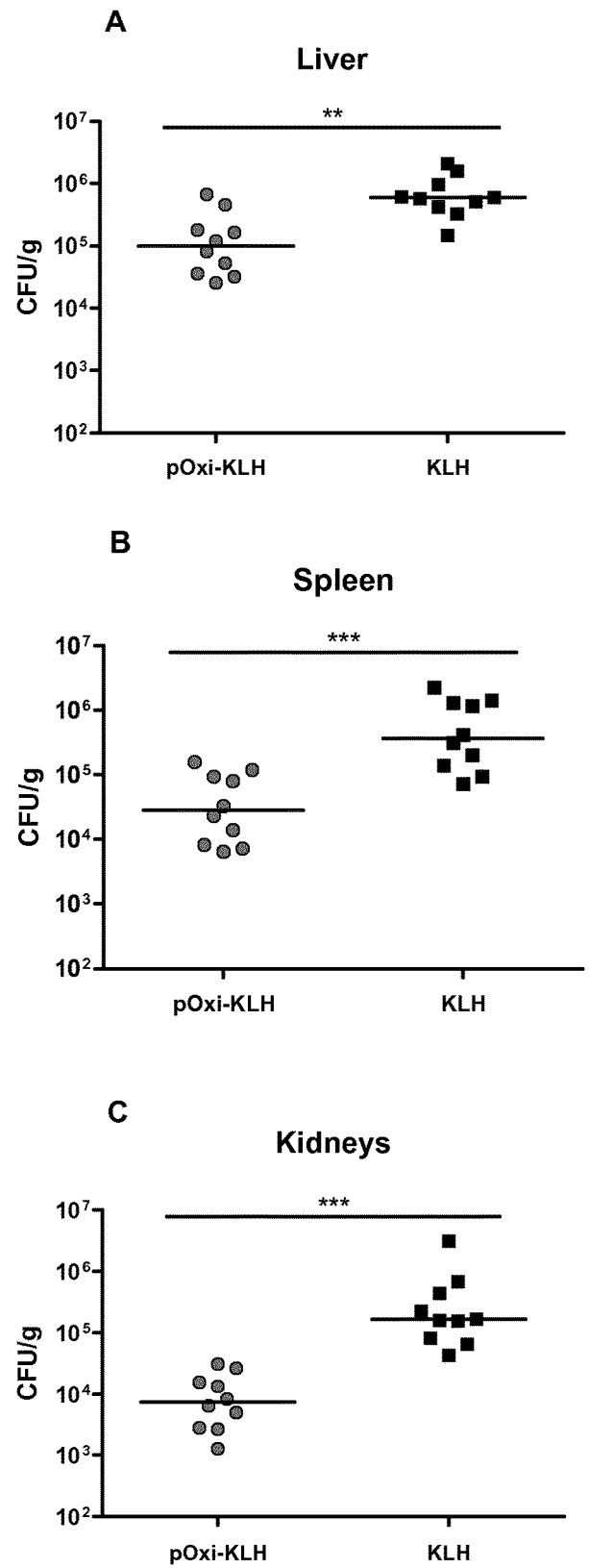

For an analysis of the bacterial load in organs of mice after challenge with *S. aureus* upon monovalent immunization with pOxi peptide (FIG. 14), BALB/c mice (n=10) were immunized with pOxi epitope peptide conjugated to KLH (blue) or with KLH (black) as a control. After the second boost mice were challenged i.p. with 4.2×10$^6$ CFU of *S.*

*aureus* USA300 mixed with 5% mucin from porcine stomach. Bacterial density of liver (A), spleen (B) and kidneys (C) was determined. P-values were analyzed by Mann-Whitney test. $p \leq 0.001 = *$; $p = 0.01 = $; $p \leq 0.05 = *$; ns=not significant.

Figure 15:
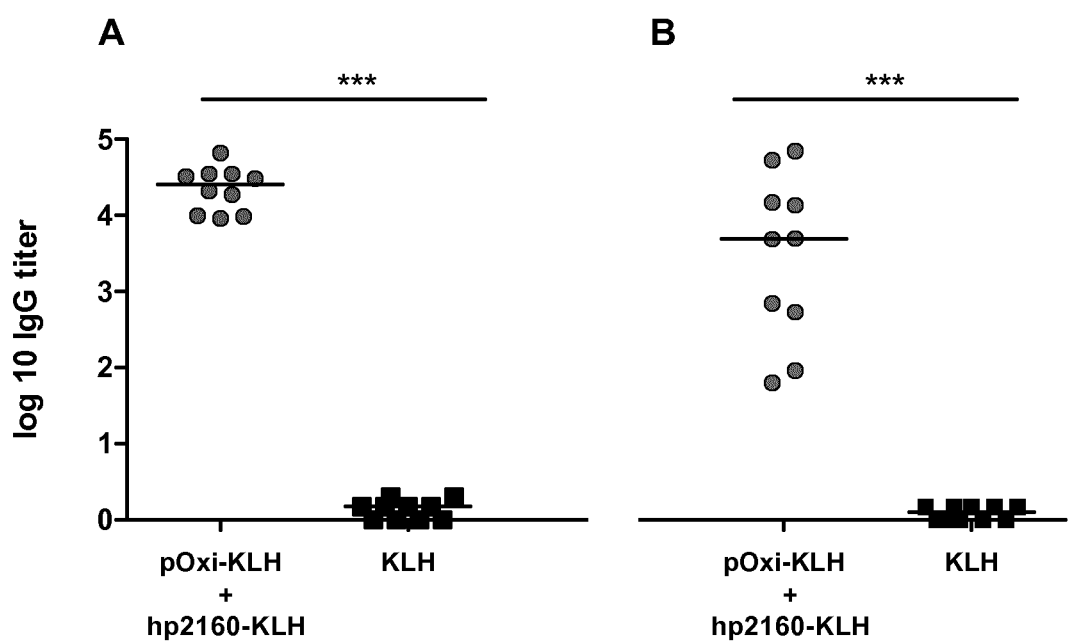

Vaccination with hp2160-KLH and pOxi-KLH Epitope Peptides Leads to High Titer Anti-pOxi and Anti-hp2160 Antibodies and Provides Protective Effect in *S. Aureus* Infection Model FIG. 15 shows the antigen-specific IgG titer after immunization with hp2160-KLH+pOxi-KLH. For this, BALB/c mice (n=2) were vaccinated with a combination of hp2160 and pOxi epitope peptide conjugated to KLH or with KLH as a control. Serum of every mouse was collected after the last booster immunization and analyzed for hp2160-(A) and pOxi-specific IgGs (B) by ELISA. The IgG titer is given as the dilution corresponding to the half maximal absorbance at 450 nm. P-value was analyzed by Mann-Whitney test: $p \leq 0.001 = ***$.

Figure 16:
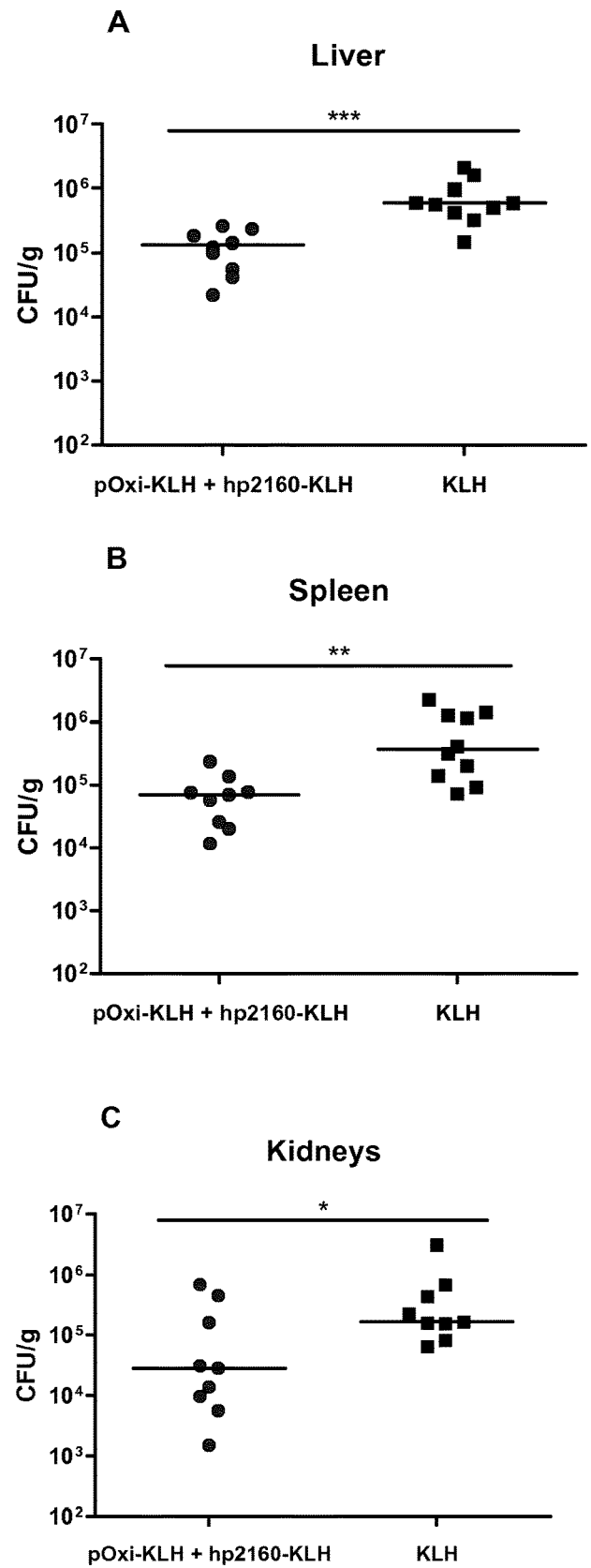

For an analysis of the bacterial load in organs of mice after challenge with *S. aureus* upon bivalent immunization with pOxi and hp2160 peptide (FIG. 16), BALB/c mice (n=10) were immunized with hp2160 and pOxi epitope peptides conjugated to KLH (dark gray) or with KLH (black) as a control. After the second boost mice were challenged i.p. with $4.2 \times 10^6$ CFU of *S. aureus* USA300 mixed with 5% mucin from porcine stomach. Bacterial density of liver (A), spleen (B) and kidneys (C) was determined. P-values were analyzed by Mann-Whitney test. $p \leq 0.001 = *$; $p = 0.01 = $; $p \leq 0.05 = *$; ns=not significant.

Figure 17:
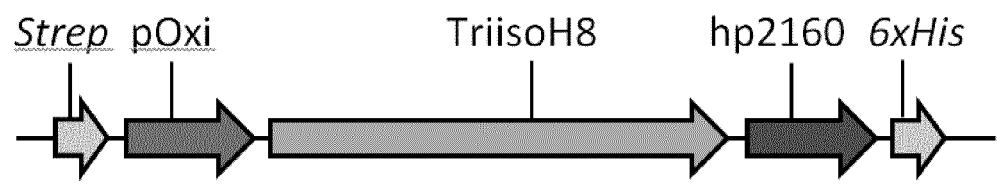

Construction of a Recombinant Triepitope Fusion Peptide-Cloning, Overexpression and Purification of Triepitope Peptide FIG. 17 shows the cloning strategy of triepitope fusion-peptide sequences encoding the epitopes of anti-pOxi moAb D3, anti-hp2160 moAb 16-2 and Triiso fragment, where epitope of anti-Triiso moAb H8 is located, were cloned consecutively, and N-terminally fused to Strep-tag, and C-terminally fused to His-tag. For the purification of triepitope peptide via His-tag, a Coomassie stained SDS-PAGE of triepitope purification via His-tag after heterologous overexpression and preparation of inclusion bodies was prepared. 15 µl of each sample and 7 µl of PAGE Ruler prestained protein ladder was pipetted on the protein gel. Purity was thus assured.

Binding Analysis of moAbs to Triepitope Peptide and its Multimeric Isoforms

Figure 18:
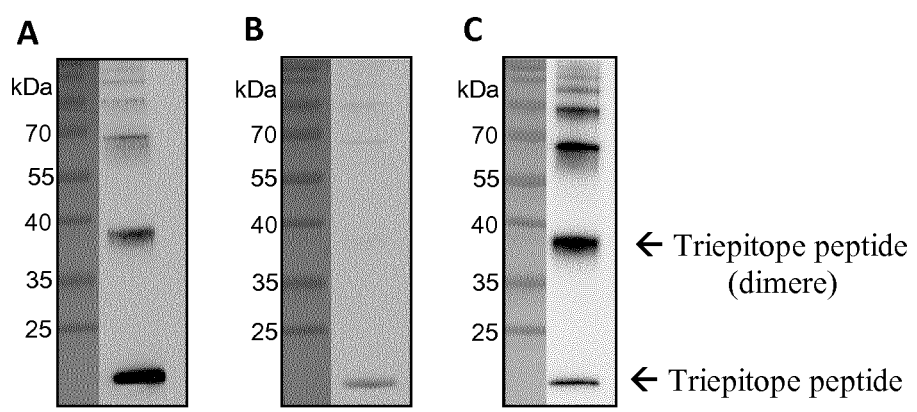

FIG. 18 shows the binding of monoclonal antibodies to triepitope peptide. For this, 10 µg of purified triepitope peptide was blotted on a nitrocellulose membrane. Membrane was incubated with anti-pOxi moAb D3 (A), anti-hp2160 moAb 16-2 (B) and anti-Triiso moAb H8 (C). Incubation with goat anti-mouse-HRP membrane followed. Membrane was developed using chemiluminescence reagent (ECL).

Immunization with Triepitope Peptide Leads to a Specific IgG Titer Against Recombinant hp2160, pOxi and Triiso and Provides Protection Against *S. Aureus* Infection in Mice For the antigen-specific IgG titer kinetic during active immunization with triepitope peptide (FIG. 19), BALB/c mice (n=2) were vaccinated with triepitope peptide conjugated to KLH and boosted twice. Blood was collected post immunization and every week after the last boost. Sera were analyzed for antigen-specific IgGs (A: anti-hp2160, B: anti-pOxi, C: anti-Triiso) by ELISA. The IgG titer is given as the dilution corresponding to the half maximal absorbance at 450 nm. Error bars indicate mean value±SEM.

Figure 20:
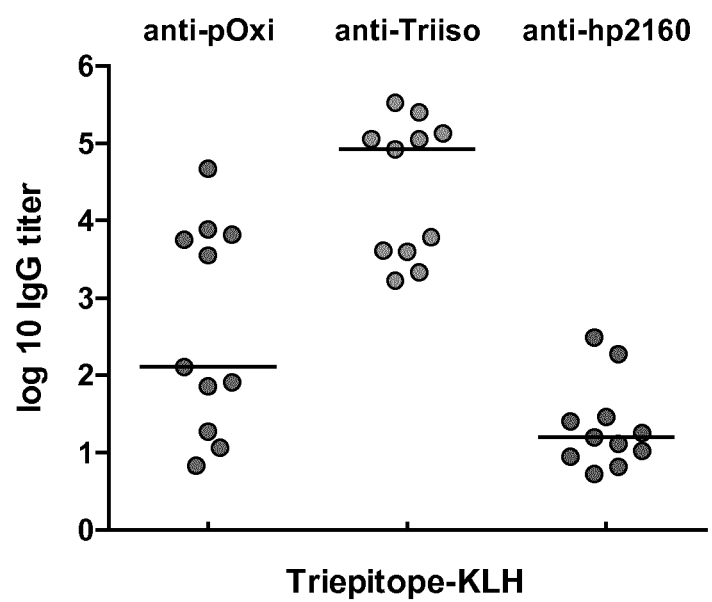

For an analysis of the antigen-specific IgG titer after immunization with triepitope-KLH, BALB/c mice were vaccinated with triepitope peptide (n=11) conjugated to KLH or with KLH (n=12) as a control. Serum of every mouse was collected after the last booster immunization and analyzed for pOxi-, Triiso and hp2160-specific IgGs by ELISA (FIG. 20). The IgG titer is given as the dilution corresponding to the half maximal absorbance at 450 nm.

Figure 21:
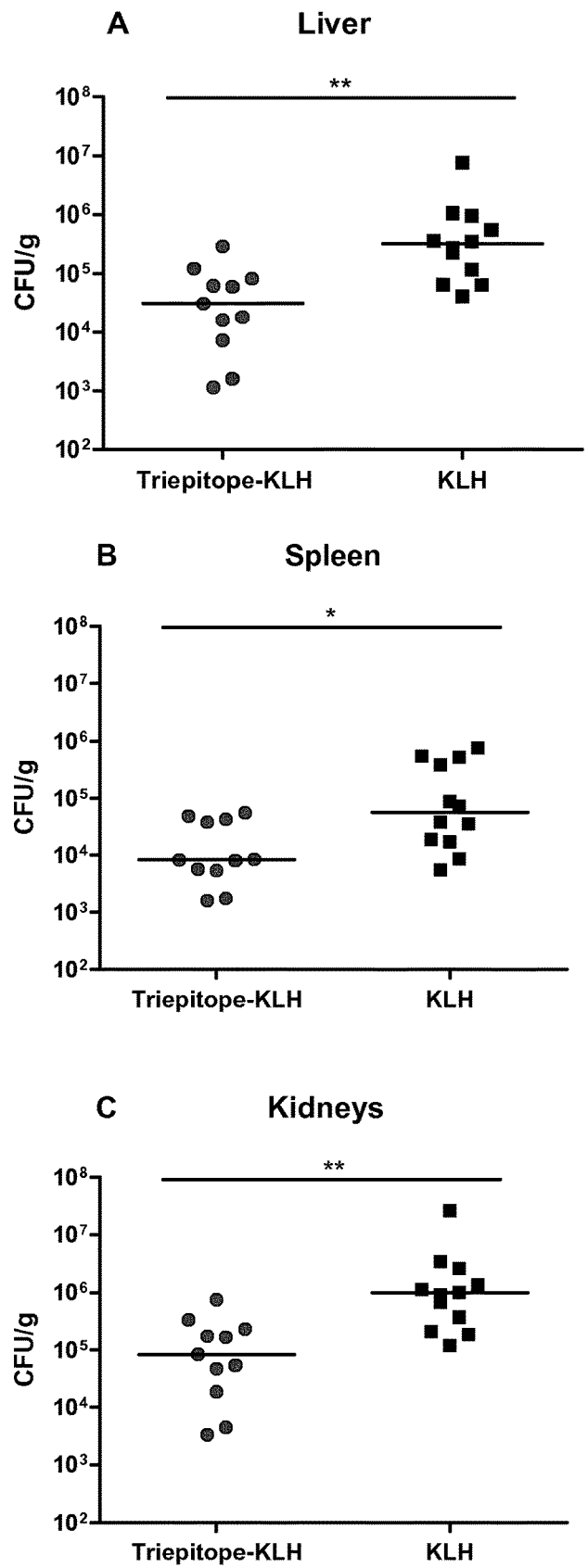

FIG. 21 shows the bacterial load in organs challenged with a sublethal dose of *S. aureus* upon triepitope peptide immunization. BALB/c mice (n=11-12) were immunized with recombinant triepitope peptide conjugated to KLH (gray) or with KLH (black) as a control group. After the second boost mice were challenged i.p. with $5.19 \times 10^6$ CFU of *S. aureus* USA300 mixed with 5% mucin from porcine stomach. Bacterial density of liver (A), spleen (B) and kidneys (C) was determined. P-values were analyzed by Mann-Whitney test. $p \leq 0.001 = *$; $p = 0.01 = $; $p \leq 0.05 = *$; ns=not significant.

Figure 22:
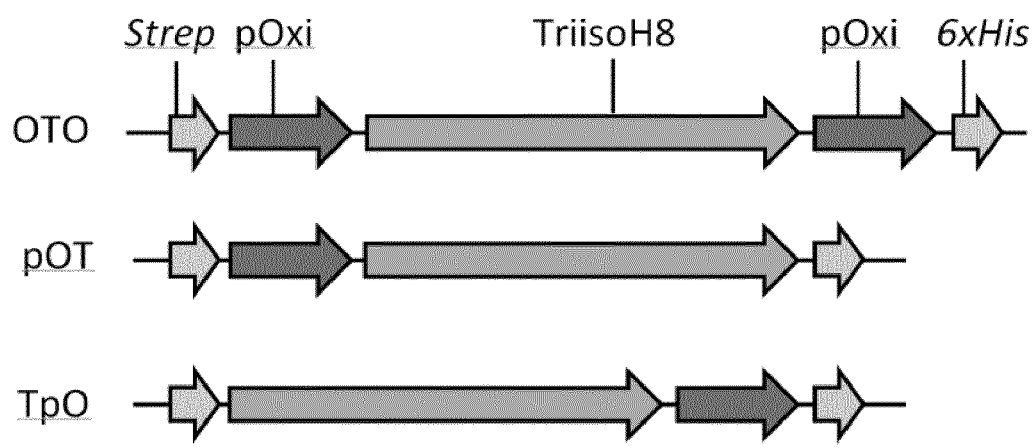

Construction of Recombinant Diepitope Fusion Peptides-Cloning, Overexpression and Purification of Diepitope Peptide The cloning strategy of diepitope fusion-peptides OTO, pOT and TpO is shown in FIG. 22. Sequences encoding the epitopes of anti-pOxi moAb D3 and of anti-Triiso moAb H8 (Triiso fragment) were cloned consecutively into pPSG-IBA43 resulting in N-terminal fusions to Strep-tag and C-terminal fusions to His-tag. OTO: Triiso fragment surrounded by C- and N-terminal pOxi epitope; pOT: N-terminal pOxi epitope; TpO: N-terminal pOxi epitope. Analysis of diepitope expression in *E. coli* BL21 revealed that TpO was not expressed (data not shown).

Figure 23:
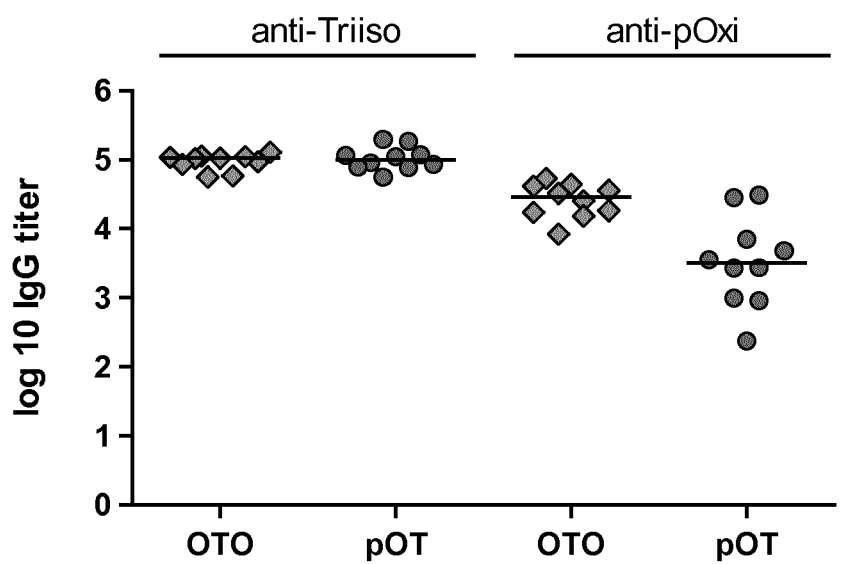

Immunization with Diepitope Peptide Leads to a Specific IgG Titer Against Recombinant pOxi and Triiso and Provides Protection Against *S. Aureus* Infection in Mice The antigen-specific immune response of mice immunized with diepitope peptide pOT and OTO is shown in FIG. 23. BALB/c mice (n=11) were vaccinated with unconjugated diepitope peptides OTO and pOT. Serum of every mouse was collected after the last booster immunization and analyzed for pOxi- and Triiso-specific IgGs by ELISA. The IgG titer is given as the dilution corresponding to the half maximal absorbance at 450 nm.

Figure 24:
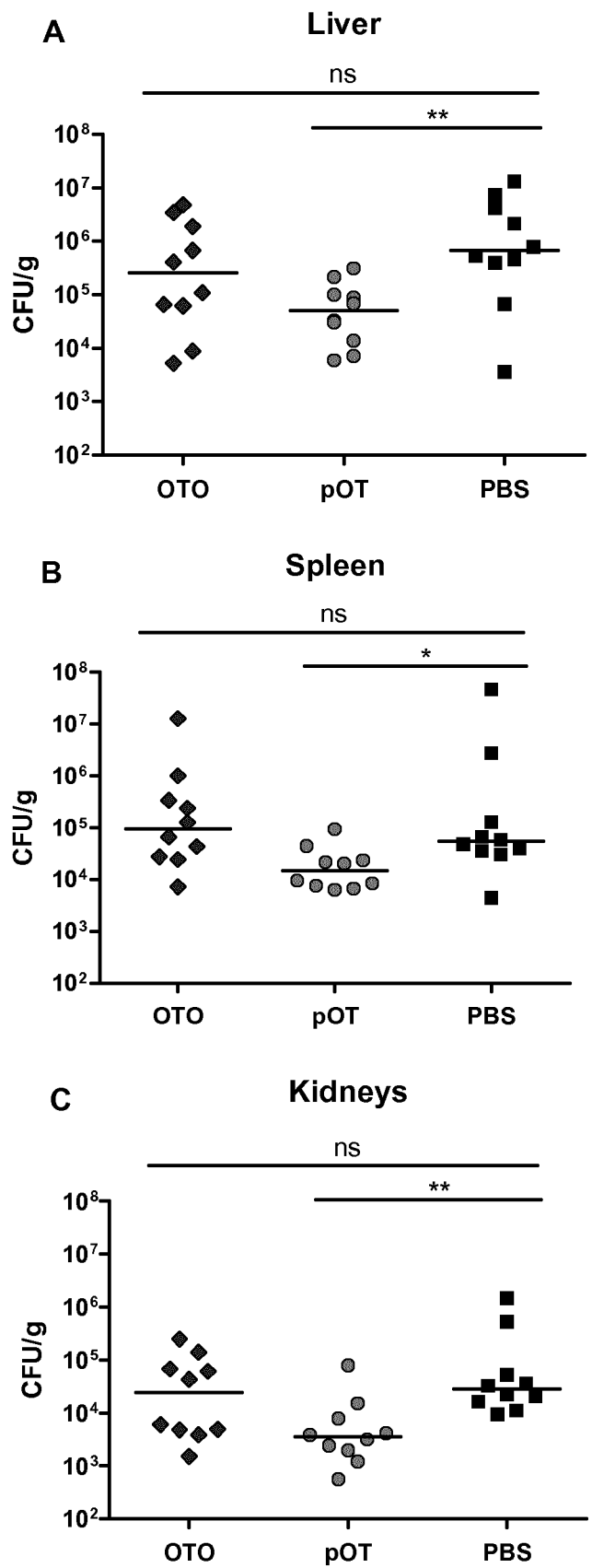

FIG. 24 shows the bacterial load in organs challenged with a sublethal dose of *S. aureus* upon immunization with diepitope peptides OTO and pOT. For this, BALB/c mice (n=10) were immunized with recombinant diepitope peptides OTO (gray) and pOT (dark gray) or with PBS (black) as a control. After the second boost, mice were challenged i.p. with $5.4 \times 10^6$ CFU of *S. aureus* USA300 mixed with 5% mucin from porcine stomach. Bacterial density of liver (A), spleen (B) and kidneys (C) was determined. P-values were analyzed by Mann-Whitney test. $p \leq 0.001 = *$; $p = 0.01 = $; $p \leq 0.05 = *$; ns=not significant.

Figure 25:
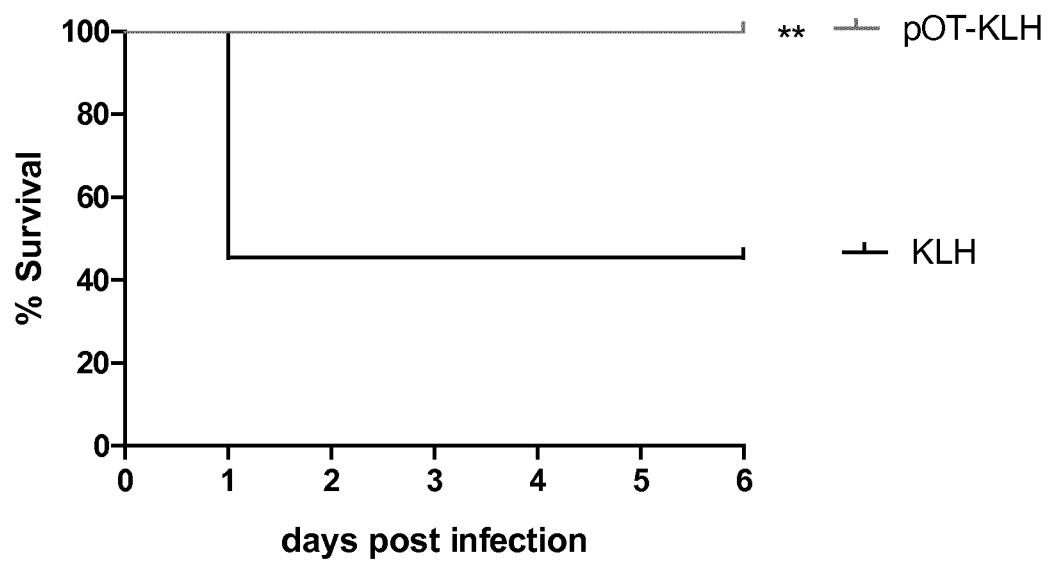

FIG. 25 shows survival of mice challenged with an $LD_{50}$ of *S. aureus* upon diepitope peptide immunization, and thus a significant protection of mice immunized with dieptiope-peptide pOT-KLH upon *S. aureus* infection. For this, BALB/c mice (n=11) immunized with pOT-KLH (gray) or KLH (black) as a control were infected i.p. with $1.2 \times 10^7$ cfu *S. aureus* USA300 mixed with 5% mucin from porcine stomach. Survival was monitored for 6 days. p-value (0.005) was determined by Gehan-Breslow test.

Figure 26:
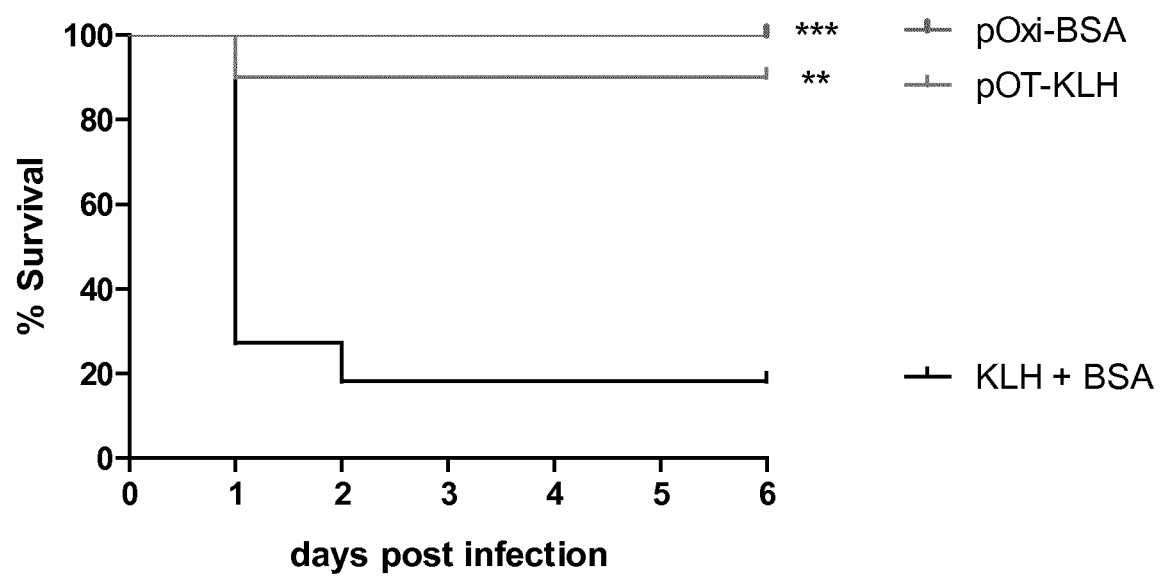
Figure 27:
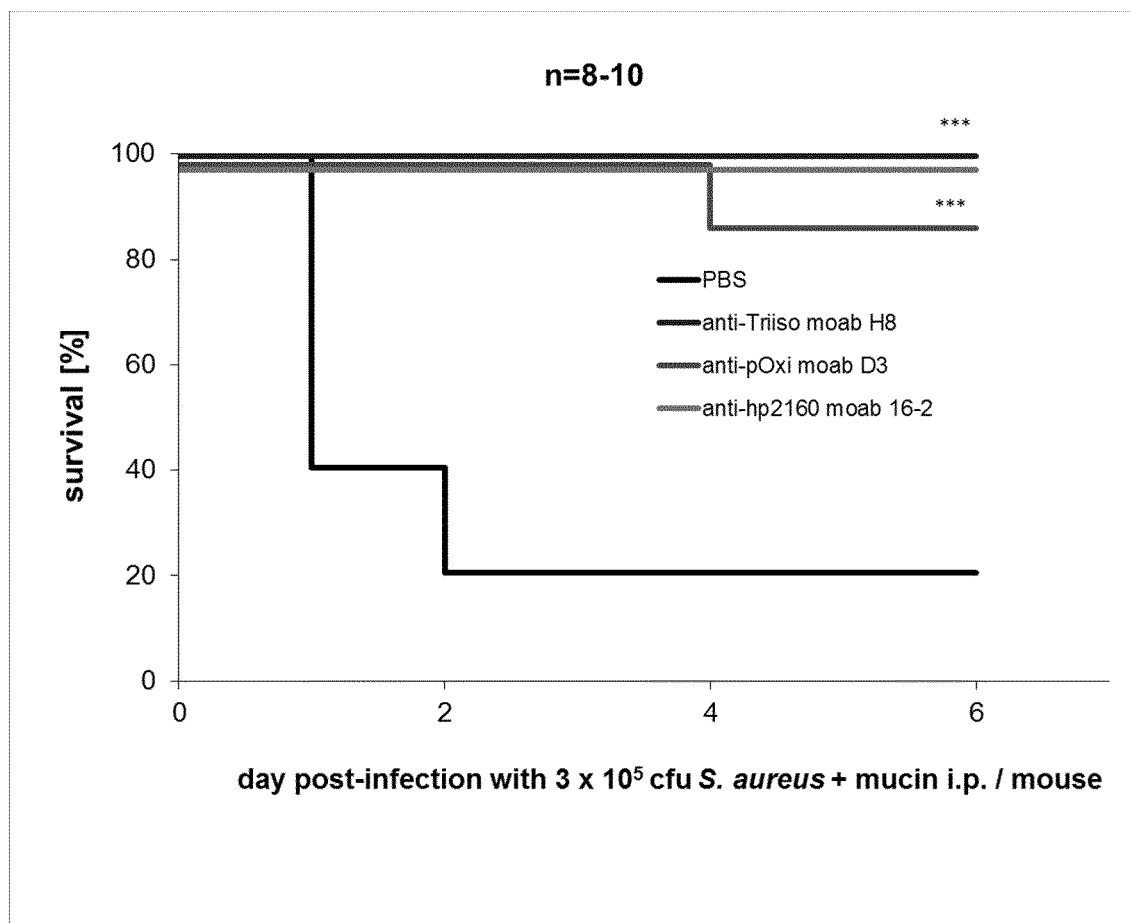
Figure 28:
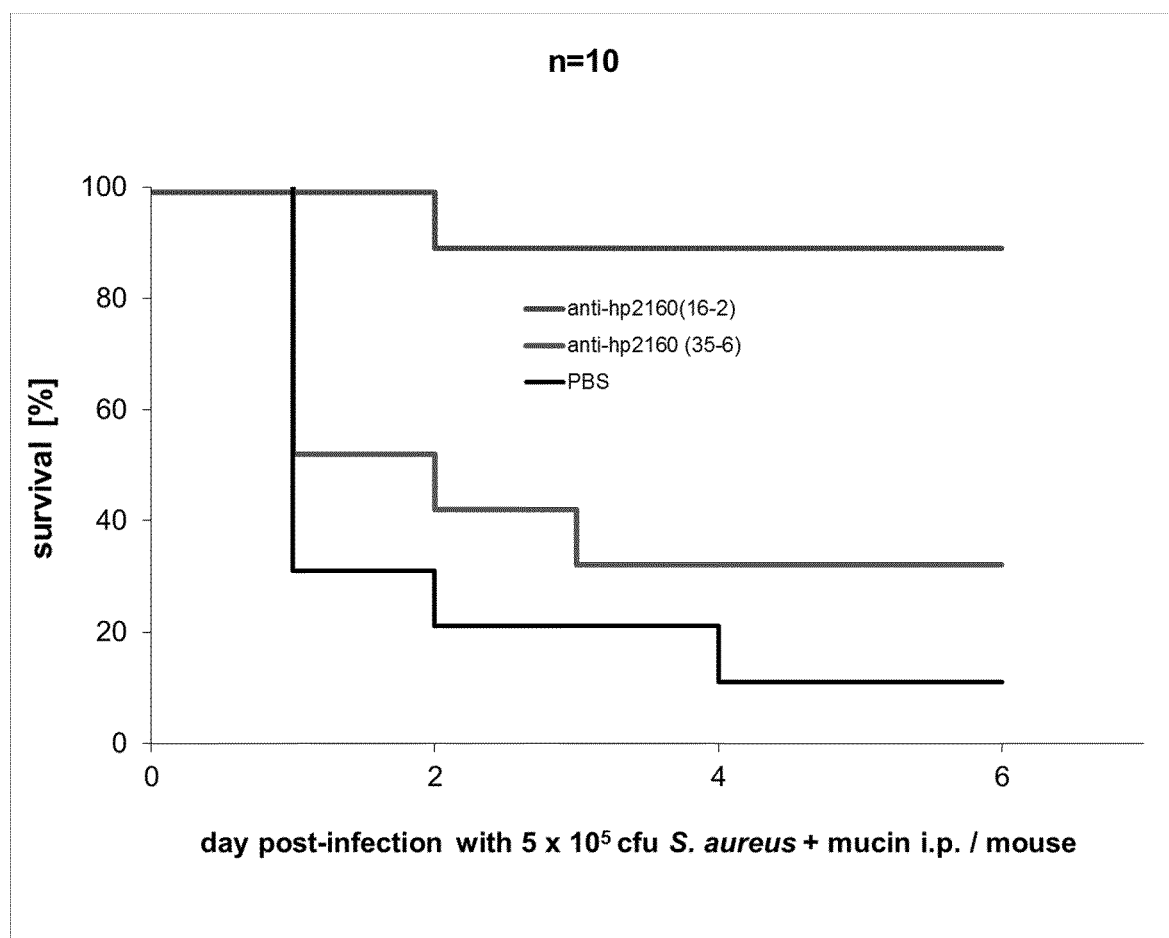
Figure 30:
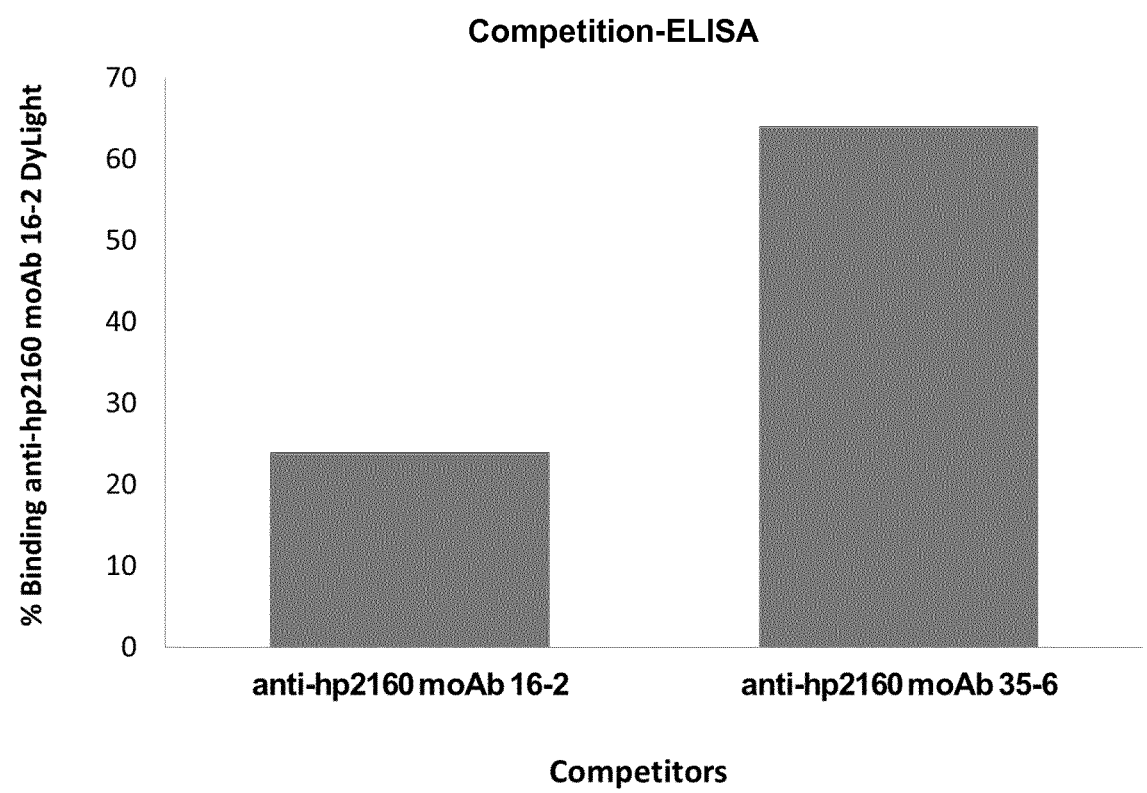
Figure 31:
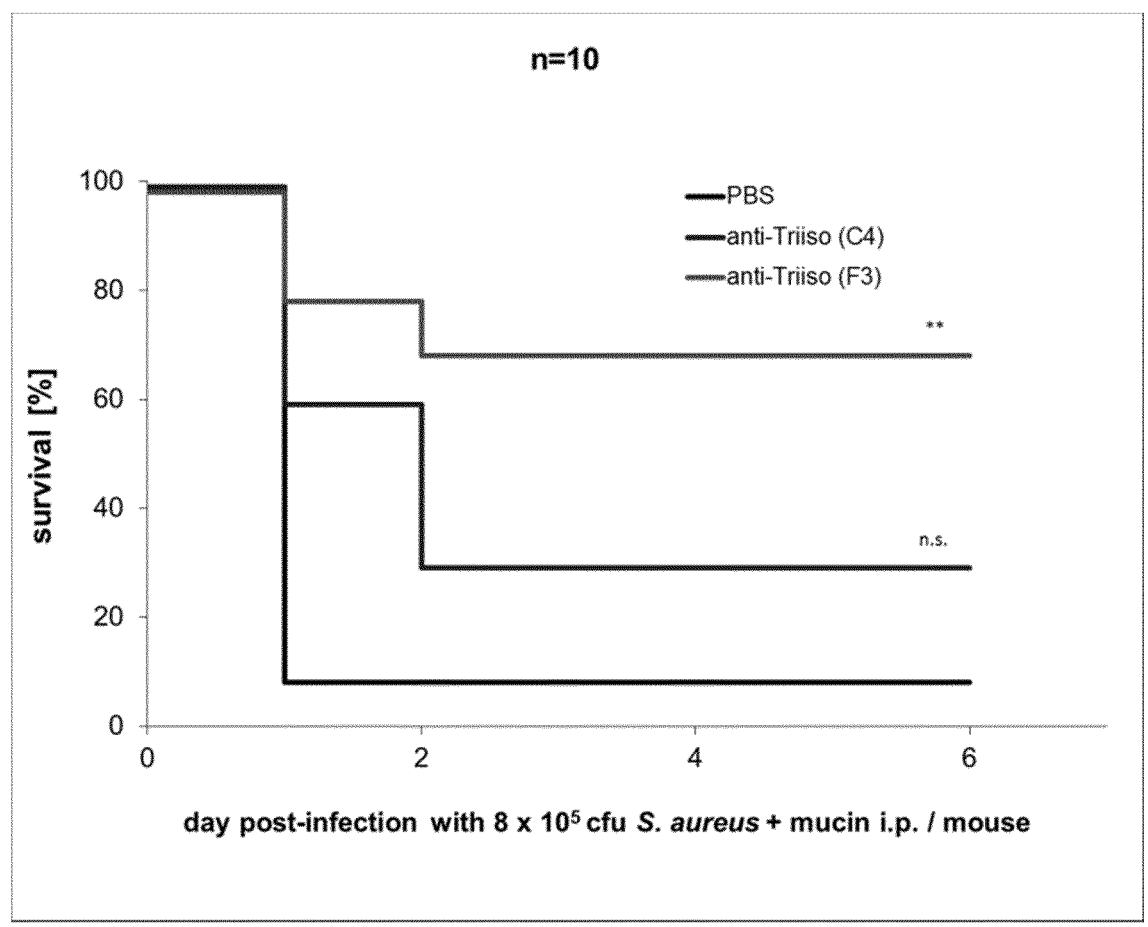
Figure 32:
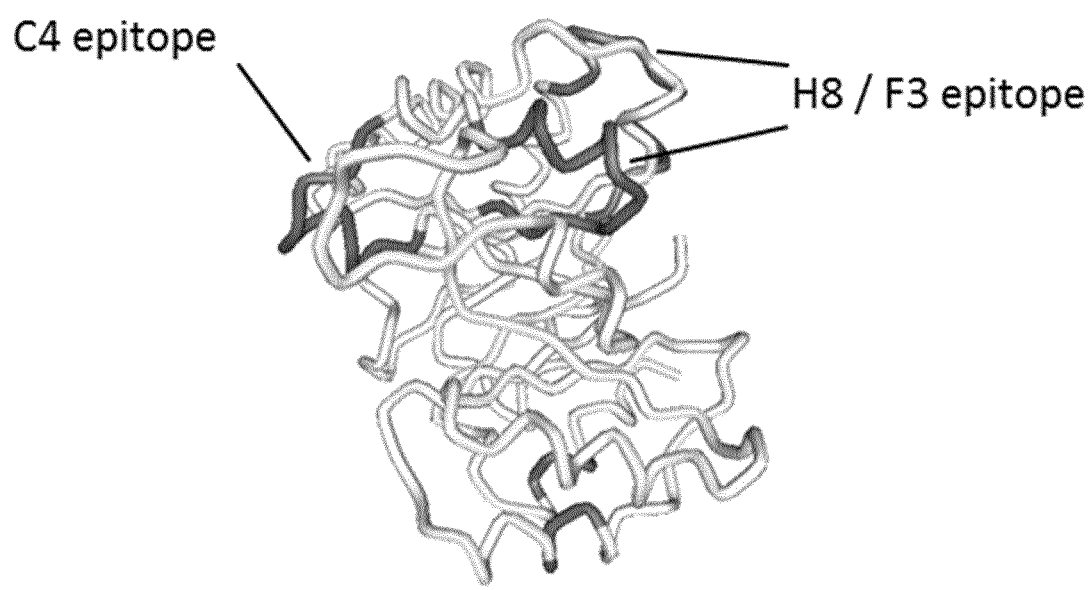
Figure 33:
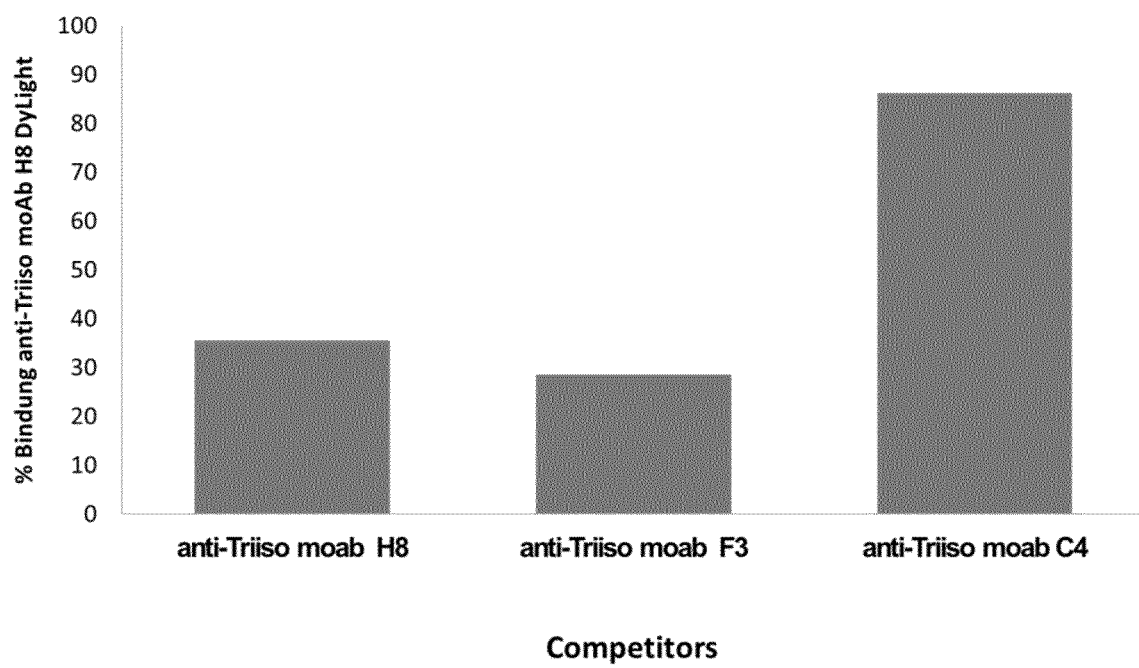
Figure 34:
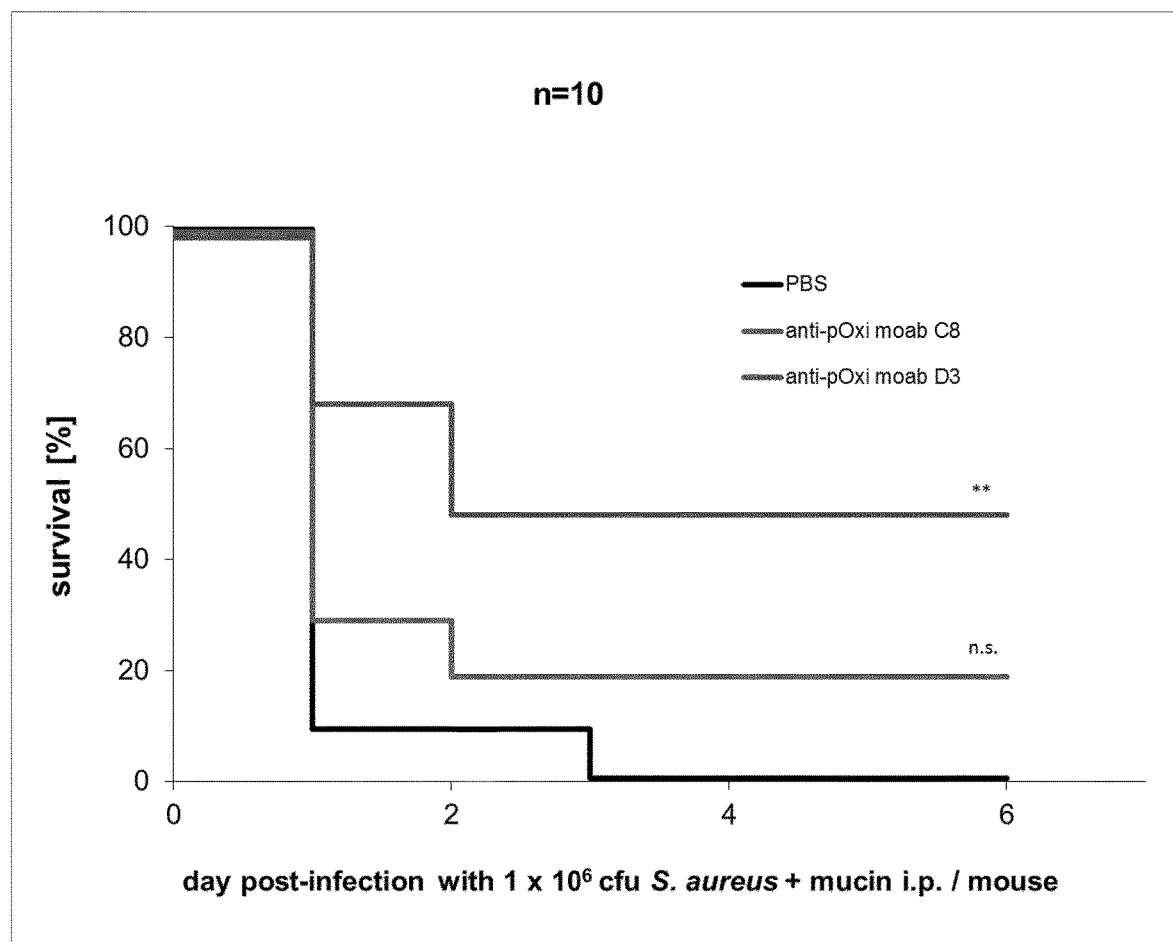
Figure 35:
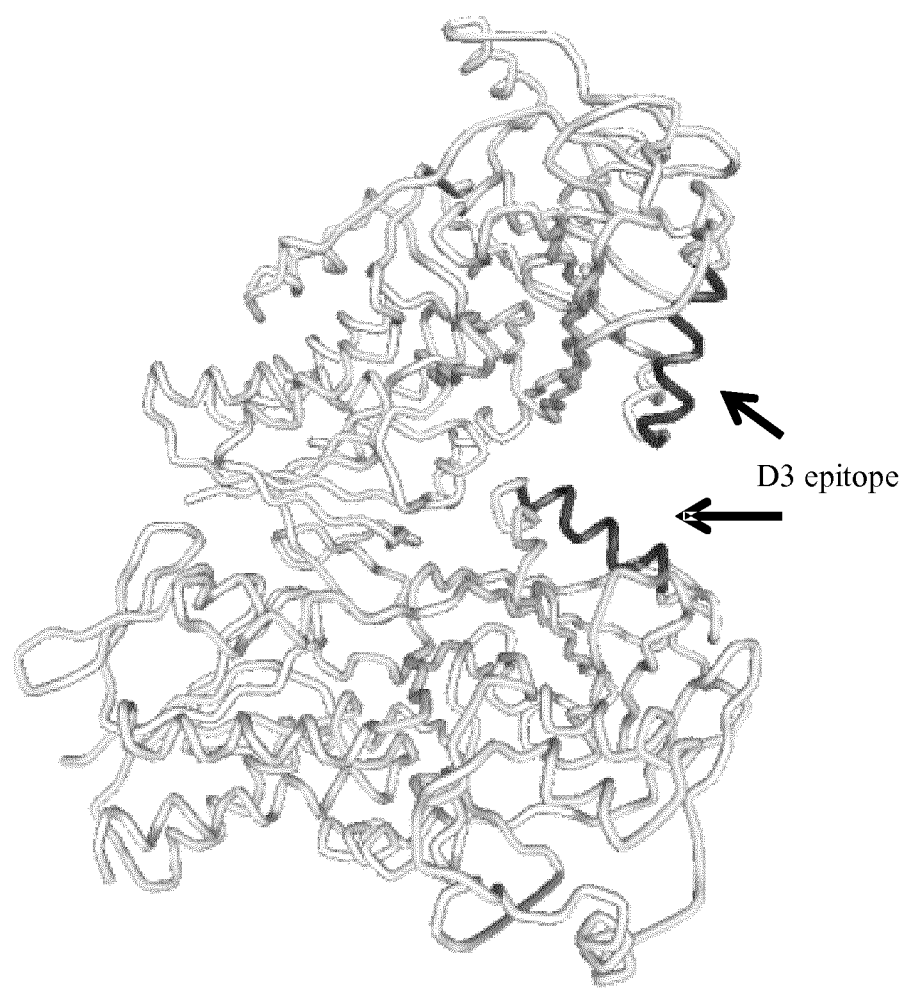
FIG. 35 shows the 3D-backbone (316D, Qin et al. 2010) of B. subtilis pOxi dimer, which resembles high homology (47% amino acid sequence) to S. aureus pOxi with anti-pOxi moAb D3 epitope (was identified by microarray technology using overlapping 13mer pOxi peptides). Anti-pOxi moAb C8 epitope is unknown but distinct from moab D3 epitope as can be concluded from FIG. 36.
Figure 36:
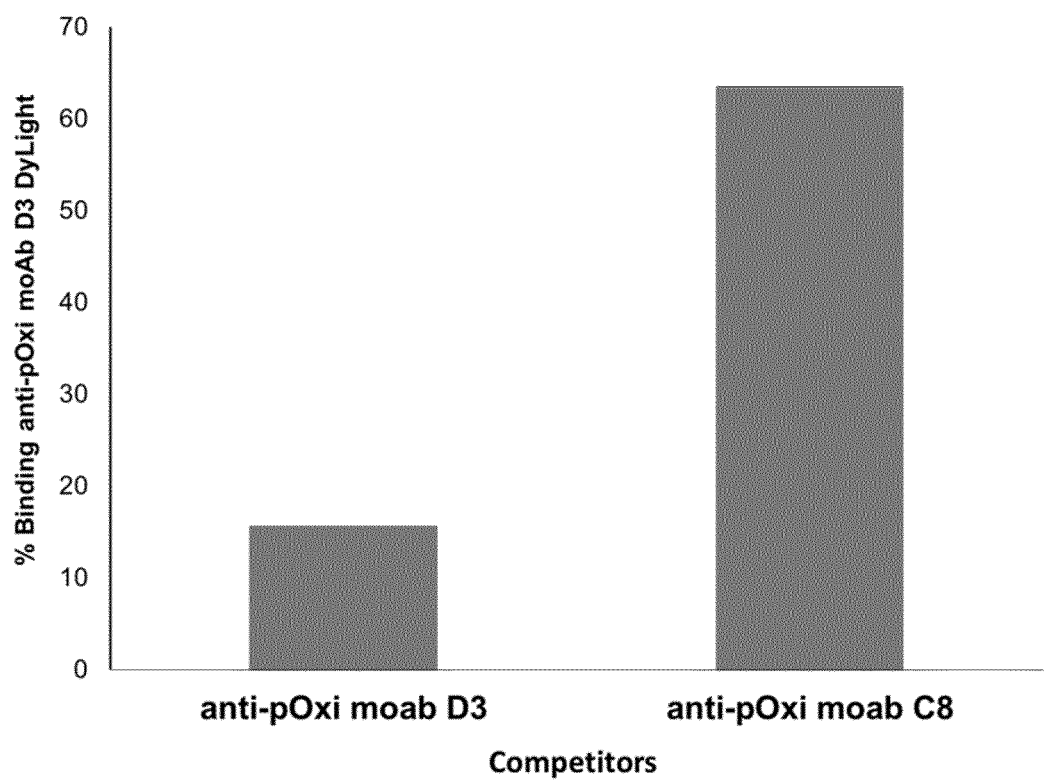
FIG. 36 shows that non-protective moAb C8 does not compete with protective moab D3 for binding to pOxi: Binding of DyLight-649 conjugated anti-pOxi moab D3 on coated recombinant pOxi was competed with unconjugated, indicated moAbs. Binding was determined by fluorescence measurement (Ex 493/Em 518) and compared to control sample (no competitor, 100% binding).

This significant protection against lethal infection with *S. aureus* is comparable with an immunization with pOxi-BSA (FIG. 26). BALB/c mice (n=11) immunized with pOxi-BSA (dark gray), pOT-KLH (gray) or a combination of BSA and KLH (black) as a control group, were infected i.p. with 3.3×10$^7$ cfu *S. aureus* USA300 mixed with 5% mucin from porcine stomach. Survival was monitored for 6 days. Given is exact p-value determined by Gehan-Breslow test.

The invention claimed is:

1. An antibody, or fragment thereof, comprising VH-CDR1: SRYWIE (SEQ ID NO: 21); VH-CDR2: EILPGSG-STNYNEKFKG (SEQ ID NO: 22); VH-CDR3: FYSGNFVGPVDY (SEQ ID NO: 23); VL-CDR1: KSSQSLSDSDGKTYLN (SEQ ID NO: 24); VL-CDR2: LVSKVDS (SEQ ID NO: 25); and VL-CDR3: WQGTH-FPFT (SEQ ID NO: 26).

2. A composition, comprising the antibody or fragment thereof according to claim 1.

3. A method comprising administering to a human or animal the composition according to claim 2.

4. A method comprising administering to a human or animal the antibody, or fragment thereof, according to claim 1.

5. A medicament comprising an antibody or fragment thereof, the antibody or fragment thereof comprising VH-CDR1: SRYWIE (SEQ ID NO: 21); VH-CDR2: EILPGSG-STNYNEKFKG (SEQ ID NO: 22); VH-CDR3: FYSGNFVGPVDY (SEQ ID NO: 23); VL-CDR1: KSSQSLSDSDGKTYLN (SEQ ID NO: 24); VL-CDR2: LVSKVDS (SEQ ID NO: 25); and VL-CDR3: WQGTH-FPFT (SEQ ID NO: 26).

6. A method comprising administering to a human or animal the medicament according to claim 5.

* * * * *